United States Patent
Bevan et al.

(10) Patent No.: US 6,913,930 B2
(45) Date of Patent: Jul. 5, 2005

(54) ANALYTICAL METHOD AND APPARATUS THEREFOR INVOLVING CONTINUOUS TITRATION

(75) Inventors: Christopher David Bevan, Stevenage (GB); Alan Peter Hill, Stevenage (GB); Derek Peter Reynolds, Stevenage (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 99 days.

(21) Appl. No.: 10/633,517

(22) Filed: Aug. 5, 2003

(65) Prior Publication Data

US 2004/0023405 A1 Feb. 5, 2004

Related U.S. Application Data

(62) Division of application No. 09/486,715, filed as application No. PCT/GB98/02711 on Sep. 9, 1998.

(30) Foreign Application Priority Data

Sep. 9, 1997 (GB) ............................................. 9719142

(51) Int. Cl.[7] .............................................. G01N 31/16
(52) U.S. Cl. ....................................... 436/163; 205/775
(58) Field of Search ........................... 436/163; 422/62, 422/68.1, 75

(56) References Cited

U.S. PATENT DOCUMENTS

| | | | |
|---|---|---|---|
| 3,484,170 A | 12/1969 | Smythe et al. | 356/181 |
| 3,732,164 A | 5/1973 | Pressley et al. | 210/752 |
| 4,120,657 A | 10/1978 | Nagy et al. | 23/230 |
| 4,810,331 A | 3/1989 | Garrison et al. | 205/780 |
| 5,192,509 A | 3/1993 | Surjaatmadja | |
| 5,447,612 A | 9/1995 | Bier | |

FOREIGN PATENT DOCUMENTS

| | | |
|---|---|---|
| EP | 0 345 782 A | 12/1989 |
| WO | 88/07196 | 9/1988 |

OTHER PUBLICATIONS

Nagy et al. "A novel titration technique for the analysis of streamed samples—the triangle–programmed titration technique. Pa I. General considerations", Analytical Chimica Acta (1977), 91(2), 87–96, Abstract.*

Araujo et al., "Single standard calibration and data processing in flow injection titration based on concentration gradients" Journal of Automatic Chemistry (1997), 19(5), 157–164, Abstract.*

C.N. Yarnitzky et al., "Automated titrations with an alternate flow: linear speed variation system", Instrumentation Science & Technology., May 2, 1995, XP000497895.

Patent Abstracts of Japan, vol. 13, No. 303, Jul. 12, 1989, JP 01 078164 A (Nippon Parkerizing, Mar. 23, 1989.

Howard Y. Ando, Tycho Heimbach, 1996, "pKa, determinations by using a HPLC equipped with DAD as a flow injection apparatus", Journal of Pharmaceutical and Biomedical Analysis.

(Continued)

Primary Examiner—Yelena G. Gakh
(74) Attorney, Agent, or Firm—Bacon & Thomas

(57) ABSTRACT

The present invention relates to an improved analytical method and apparatus therefor, in particular to a method and apparatus for continuous titration in which at least one parameter of at least one compound in a test mixture may be monitored as the composition of the mixture is continuously varied. The method comprises the steps of continuously mixing at least two component fluid streams to form a test mixture stream and passing the test mixture stream through a spectrophotometric detection zone, with the volume to volume ratio of at least two of the component streams forming the test mixture stream continuously and linearly varied with time by alteration of the relative proportions of the component streams forming the test mixture, while the total volume of the test mixture stream remains constant.

17 Claims, 24 Drawing Sheets

OTHER PUBLICATIONS

Lars Norgaard, "Determination of pH gradients and acidity constants in flow–injection analysis systems by evolving factor analysis", 1991, Analytica Chimica Acta, Elsevier Science Publishers, B.V.

Japanese Abstract, JP05126791–A, May 21, 1993, Agency of Ind Sci & Technology, (MITB) Mitsui Eng & Shipbuilding Co.

Ari Ivaska, "Rapid Determination of the Equivalence Volume in Potentiometric Acid–Base Titrations to a Present pH–1", Talanta, vol. 21, pp. 377–386, 1974.

Ari Ivaska, Rapid Determination of the Equivalence Volume in Potentiometric Acid–Base Titrations to a Present pH–II* Standardizing a Solution of a Strong Base, Graphic Location of Equivalence Volume, Determination of Stability Constants of Acids and Titration of a Mixture of Two Weak Acids, Talanta, vol. 21, pp. 387–392, 1972.

Johansson et al., "Single–Point Titrations Part I. The Determination of Bases", Analytica Chimica Acta, 69(1972), pp. 415–424.

Ove Astrom, "Single–Point Titrations Part II. Experimental Determination of Bases", Analytica Chimica Acta, 88, 1977, pp. 17–23.

Ove Astrom, "Single–Point Titrations Part III. Experimental Determination of Acids", Analytica Chimica Acta, 97, 1978, pp. 259–267.

Fleet et al., "Gradient Titration–A Novel Approach to Continuous Monitoring Using Ion–Selective Electrodes", Analytical Chemistry, vol. 46, No. 1, Jan. 1974.

* cited by examiner

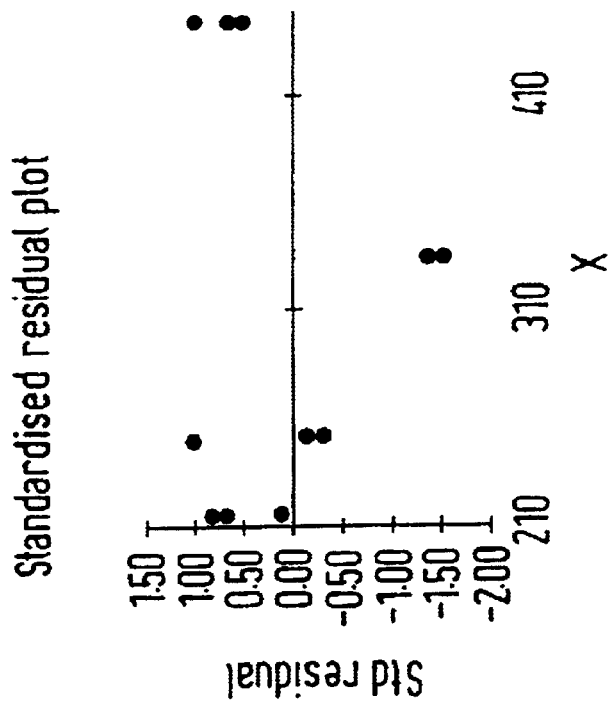
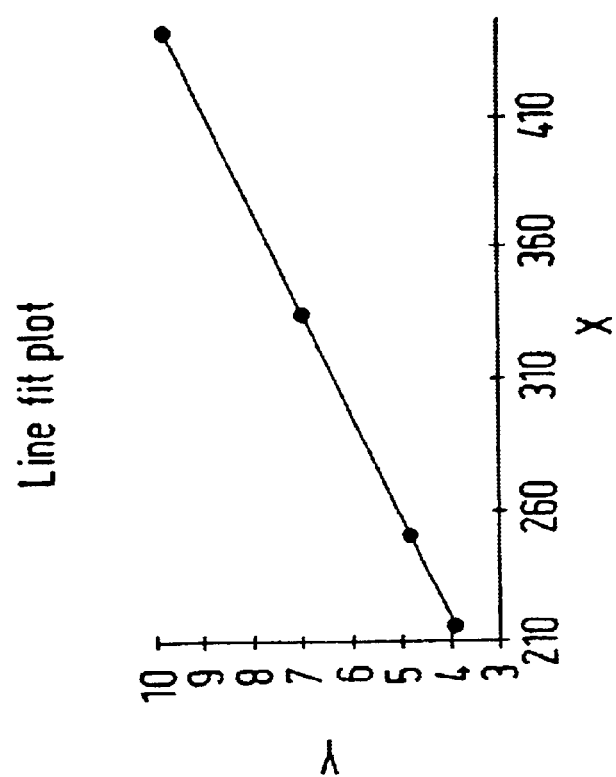
FIG. 12

Time = 361.3 seconds
pH = 7.64

FIG. 16 Absorbance curve for an endpoint titration (KHP at 240nm)

ANALYTICAL METHOD AND APPARATUS THEREFOR INVOLVING CONTINUOUS TITRATION

CROSS REFERENCE TO RELATED APPLICATIONS

This application is a divisional application of pending U.S. application Ser. No. 09/486,715, filed May 24, 2000 (of which the entire disclosure of the pending, prior application is hereby incorporated by reference), which is a 371 of PCT/GB98/02711, filed Sep. 9, 1998.

The present invention relates to an improved analytical method and apparatus therefor, in particular to a method and apparatus for titration.

Many compounds have physicochemical properties which vary according to their chemical or physical environment, which properties can be investigated by changing that environment and observing the effects on the test compound. Examples of such properties are ionisation state, solubility, partitioning between e.g. organic and aqueous phases or into micelles or liposomes, the strength of ligand binding or metal complexing and hydrophobicity, which can vary with environmental parameters such as pH, ionic strength, or the concentrations of other species in the system. Analytical chemists studying the properties of chemical or biological molecules have long counted titration amongst the major tools of their trade as it allows one parameter of a system, e.g. the pH of a solution, to be varied by dropwise addition of one or more reagents whilst other parameters of the system remain essentially constant, allowing the effects of the variation to be studied effectively in isolation.

An example of a property which can be determined by titration is the pKa (or dissociation constant) of an ionisable group of a compound, which can be defined as the pH at which the group is 50% ionised. The level of ionisation of a given ionisable group at any pH can be directly calculated once the pKa is accurately known. A given molecule may have multiple pKas if it contains more than one ionisable group. As a molecule's state of ionisation can alter other properties such as hydrophobicity and aqueous solubility, knowledge of the pKa(s) of a potential drug molecule is of great importance. To date, because of difficulties with traditional titrimetric techniques, pKa information has not been utilised to the full. Hereinafter, general principles and techniques are discussed in relation to a range of physicochemical properties which may be ascribed to a test compound. Where pKa is discussed, for simplicity it will be assumed that a molecule has only a single ionisable group and therefore a single pKa, however the discussion will apply equally to molecules exhibiting multiple pKas. Where the existence of multiple pKas is of particular significance, this will be addressed specifically.

Traditional titration techniques suffer from many disadvantages. They are slow, at most a small number of samples can be tested per man-day. They are labour intensive, with each dropwise addition of reagent followed by a delay for the mixture to equilibrate before the taking of a reading. The accuracy of conventional techniques is limited by the size of drops added, which can vary with the skill of the operator, and also the concentration of the test compound is altered as each dropwise addition of a reagent dilutes the test sample. Furthermore, relatively large amounts of test compound are required for standard titrimetric techniques, for example if the titrimetric analysis is to determine the pKa of a compound and is monitored by a UV spectrophotometer then 1 mg of test compound may be required. If the same analysis is monitored by a pH meter over 3 mg of the compound may be required. Generally spectrophotometric titrations are not automated, whilst potentiometric titrations have been, but even recent attempts at automation have provided slow (1–5 compounds per day), discontinuous techniques and have not removed the need for a skilled laboratory technician to be on hand.

One automated titration system is described by Yarnitzky (Instrumentation Science and Technology, Vol. 23(2), 91–102 (1995) using two peristaltic pumps, a mixing coil and two three-way valves. The system requires the pump drivers to be accurately matched, uses conductimetric or potentiometric detection, and requires compensation for tubing deterioration caused by the pumps, the delay of the mixing coil and the response time of the detector. Ando and Heimbach (J. Pharmaceutical and Biomedical Analysis 16 (1997), 31–37) describe the use of an HPLC instrument as a mixer and pump to deliver a succession of samples, each buffered at a different pH, to a spectrophotometric detector.

In the pharmaceutical industry, as in other branches of chemistry, the current trends towards combinatorial chemistry and recombinant genetic engineering are producing ever more new compounds, ever more quickly. In the pharmaceutical industry, there is a need for the suitability of these new compounds as potential drugs to be evaluated quickly. Several hundred pKa determinations per day may be desirable. The amounts of each compound available for testing may be very small. Consequently there is a need for a more sensitive technique, which can preferably be easily automated for a higher throughput, and which can preferably be operated by laboratory chemists without special training.

Accordingly, the present invention provides a method of continuous titration in which at least one parameter of at least one compound in a test mixture may be monitored as the composition of the mixture is continuously varied. The continuous variation may be characterised by changing concentration of one or more species or components in the mixture, for example a continuous, preferably linear increase or decrease in the concentration of the species or component.

In the present method at least two fluid streams are continuously mixed to form a test mixture stream which passes through a spectrophotometric detection zone. The volume to volume ratio of at least two of the component streams in the mixture entering the detection zone is continuously variable with time by alteration of the relative proportions of the component streams forming the test mixture. Preferably, three or more component fluid streams are continuously mixed to form the test mixture stream, the volume to volume ratio of two of these component streams being continuously varied with time by alteration of their relative proportions in the forming of the test mixture.

In traditional potentiometric and conductimetric titrations, the response time of the detector is often the rate limiting step. The use of spectrophotometric detection considerably speeds the titration process, and spectrophotometric detection is preferred here.

The present method has the further advantage that, as solutions are not added dropwise but are continuously mixed in varying proportions, the accuracy is no longer limited by the size of drops added. Furthermore, the process can be speeded up considerably; as mixing is continuous, there is no waiting time whilst the mixture equilibrates after addition of each drop. The limiting step may then be the flow rate achievable through the pumps, mixers and tubes used. A further advantage of the present method is that it can better take advantage of the rate of data sampling at the detector which, in a modern instrument such as a diode array spectrophotometric detector with fixed geometry optics, can be very high e.g. 100 readings per second may be possible although in practical embodiments, 10–30 readings per second, e.g. 20 per second may be taken. High data sampling rates allow the option of "data smoothing" or noise reduction. For example if 20 readings per second are taken, these can be averaged over 10 readings to give an effective sampling rate of 2 per second. This averaging can provide more sensitive detection than conventional methods of spectrophotometric detection.

Thus, in certain embodiments, the present invention provides a method of continuous titration in which a flowing fluid stream comprising a compound under test is mixed with at least one additional flowing fluid stream to form a test mixture stream and the test mixture stream is passed, preferably at a constant flow rate, through a spectrophotometric detection zone at which readings relating to at least one physical or chemical parameter of the compound under test may be taken. Preferably, the test mixture stream is mixed from three fluid components; the first, the volume of which preferably remains constant as a percentage of the total volume of the test mixture stream, comprises the compound under test. The concentration of this compound in the mixture stream therefore remains constant. The % volumes of the second and third components are preferably variable in inverse proportion to one another; as the % volume of one rises, the % volume of the other falls, so as to keep the total volume of the mixture constant. The variable components may comprise buffer solutions, solvents, test reagents, organic and aqueous phases or other fluid components which may be varied relative to one another to alter the physical or chemical environment of the compound under test. Optionally, further fluid components may be included in the test mixture, at constant or variable volume. For example, salt solutions may be employed to maintain a chosen ionic strength, indicators may be added or the amount of water (or other solvent) may be adjusted to compensate for changes made to the volume of other fluid components.

In especially preferred embodiments, the variable components comprise two linearising buffers—that is two buffers whose relative proportions may be altered to produce a linear pH gradient. These buffers will desirably be formed from components such as an acid and a basic salt of the same compound so that the overall chemical composition of the mixture remains constant during titration and no additional ionic species are introduced. This uniformity of chemical environment gives a measure of predictability to the behaviour of compounds introduced into the titration system, as the behaviour of some compounds can alter if the chemical environment changes significantly even, in rare cases, leading to the compound precipitating from solution as a solid salt forms.

Thus in one embodiment, in which the pKa of a test compound is to be determined, a test mixture stream is formed from three components: a constant volume of sample solution and two linearising buffer solutions the volumes of which vary in inverse proportion to one another. The absorbance is measured (at one or more wavelengths, at least one of which will be a wavelength at which there is an absorbance difference between the ionised and unionised forms of the compound) as the proportions of the buffers are varied to produce a linear pH gradient. The pKa of the test compound is the pH at the mid-point of the absorbance change. If the test compound has more than one ionisable group, more than one absorbance change may be observed. The mid-point of the second change then corresponds to the pKa of the second ionisable group.

In a second aspect, the present invention provides an analytical device comprising at least two input ports in fluid communication with a common channel, and a detection zone having an input in fluid communication with the common channel and an output, the device further comprising a spectrophotometric detector for monitoring fluid flowing through the detection zone and producing data relating to at least one chemical or physical characteristic of a component of the fluid. Control means may be associated with the input ports for controlling the relative amounts of fluid introduced into the common channel through each port.

The detector may be any suitable spectrophotometric (i.e. radiation-detecting) analytical detector e.g. an ultraviolet or visible range spectrophotometer, a fluorimeter, a polarimeter, a colourimeter, or a light scattering, optical rotation or circular dichroism detector.

The control means for controlling the relative amounts of fluid introduced into the common channel through each port may be e.g. a pump controller such as is commonly used with HPLC instruments. Alternatively, one or more of the input ports may have associated with it a syringe by which a fluid may be introduced through the port into the common channel, the plungers of the syringes being moved mechanically under the control of e.g. a computer. The skilled man will be able to envisage other means by which the input of fluids into the common channel may be controlled, such that the proportions of the fluids making up the test mixture and the rate of flow of the test mixture along the common channel through the detection zone may be controlled. The use of syringe pumps or pump mixers based on those employed in HPLC instruments, in combination with small-bore tubing and microanalytical detectors in-line, such as fixed geometry optics spectrophotometers, means that very small volumes of test mixture may be used. Consequently, smaller quantities of test compound are needed than were required for traditional titration methods. Automatic syringes have, in particular, the advantages of low dead volume (avoiding the dead volume of a separate pump) and being easily programmable for automation.

In one preferred embodiment, an HPLC mixer pump is connected to reservoirs of each fluid component of the test mixture. The mixer pump takes the fluid containing the test compound at a constant rate and mixes it with a first buffer solution pumped at an increasing rate and a second buffer solution pumped at a decreasing rate, so that the total volume and flow rate of the resulting mixture remains constant, but the relative amounts of each component of the flowing mixture change over time. The changing proportions of the two linearising buffer solutions in the mixture preferably result in changing the pH of the mixture as a whole and are desirably controlled to give a linear pH change over time. Such a system may be used to determine e.g. the pKa(s) of a test compound.

In another embodiment, an autosampler carousel contains reservoirs of a number of solubilised compounds to be tested, and a number of automatic syringes each contain a reservoir of one other fluid component of the test mixture, for example a first and a second buffer solution. The first buffer solution is then pumped at an increasing rate from a first automatic syringe to a mixing chamber and a second buffer solution is pumped to the mixing chamber at a decreasing rate, so that the total volume and flow rate of the resulting mixture remains constant, but the relative amounts of each component of the flowing mixed buffer stream change over time. The changing proportions of the two linearising buffer solutions in the mixture preferably result in changing the pH of the mixture as a whole and are desirably controlled to give a linear pH change over time. The autosampler takes a sample of fluid containing one of the test compounds and injects it, at a constant rate, into the mixed buffer stream to form the test mixture stream, which passes through the detector. Such a system may be used to determine e.g. the pKa(s) of a test compound.

The nature and number of fluids mixed to form the test mixture will depend upon the analysis to be performed. For example, if the partition coefficient of a molecule is to be determined, the flow rate into the apparatus of the fluid containing the test compound may be kept constant and those of the two phases between which the molecule will partition may be varied, preferably inversely and linearly. Examples of phase partition fluids which may be employed include oil-in-water emulsions or emulsions of other organic solvents in aqueous solvents (e.g. octanol in water), surfactant micelles (e.g. sodium dodecyl sulphate (SDS) micelles) and phospholipid, e.g. DMPC liposomes, but the skilled man will be able to select an appropriate mixture to suit the test compound, from his own knowledge. Alternatively, a linear pH gradient test mixture stream may be formed as discussed above and brought into contact with a flowing organic phase (e.g. octanol) stream, for example using a microscale chemical processing device being developed by CRL (Central Research Laboratories Ltd., associated with EMI Group plc) and BNFL (British Nuclear Fuels Limited). This device is specifically designed to allow aqueous and organic phases to flow in contact with each other and then be clearly separated. Details may be found in "Eureka, Transfers Technology" October 1997, page 42. From the difference in the pKa of the test compound with and without contact with the organic phase, the partition coefficient may be calculated.

If the parameter to be determined is the binding coefficient of a test compound with a second molecule or other reagent, then the fluids whose proportions are to be varied may include one or both of the binding reagents themselves, and/or salt solutions or buffers for controlling the ionic strength and/or pH of the mixture. For example, test solute may be introduced in the manner discussed above, as a constant proportion of the test mixture. Rather than pH being varied as a function of time by the mixing of e.g. two buffers, the ligand of interest is titrated against water or a solvent of relevance in the presence of solute, thus giving a continuous, preferably linear, gradient of ligand concentration. An example of such a system is nickel(II):Ethylenediamine. Possible interactions which could be studied using the techniques and apparatus of the present invention include those between enzymes and their substrates or cofactors, chelators and metal ions, receptors and their agonists or antagonists, antibodies and their antigens, or the strength of interaction in any form of complex or specific binding pair. The data produced could be analysed using traditional techniques. This approach could be advantageous over other approaches as no dilution factor need be corrected for.

If a compound's solubility in different solvents is being studied, then the levels of two or more different solvents may be adjusted and the effects on the test compound observed. Other examples will readily occur to the skilled man.

In certain embodiments, the automatic syringes, or reservoirs and mixer pump, discussed above may be replaced by other pumping systems which can handle very small volumes with high precision and accuracy. Other suitable pumping systems include peristaltic pumps (although these may lead to pulsing of the pumped mixture) and digital on-off valve pumps in microtubing. Of course the apparatus may comprise two or more different sorts of pump. Where a mixer pump is not employed, desirably some other means of efficiently mixing the components of the test mixture stream will be used, for example a mixing coil, a mixer T-piece or a spin-mixer.

As discussed above, where a molecule has a single ionisable group and the ionised and unionised forms have different UV absorbance spectra, an absorption change will be detected as the mixture of ionised and unionised forms changes from predominantly ionised to predominantly unionised (or vice versa). See the generalised diagrammatic representation of FIG. 11 and, for a practical example, FIGS. 14 and 15. For such a single ionisable group, the pH corresponding to the mid-point of the change in absorbance is the pKa of the compound (the pH at which 50% of the molecules are ionised). The mid-point (inflexion point) of this curve can be determined by curve-fitting, or by taking the 1st derivative of the absorbance readings against pH, which gives a peak corresponding to the point of inflexion. Use of the first derivative plot allows pKas which lie close to the ends of the pH gradient to be determined, as the gradient need only run a short way past the inflexion point for the first derivative plot to peak and begin its down-turn. By contrast, the inflexion point of the curve-fitted absorbance trace can only easily be determined if the lowest and highest absorbance levels can be seen on the trace, which requires a longer span of the pH gradient, as can be seen from FIG. 11.

For a one step ionisation process, the pH at the point of inflexion, or at the peak of the first derivative plot, is equivalent to the pKa. Irving et.al. Analyst 80, 83–94 (1955) suggested the use of the first derivative method to determine the pKa values for processes involving two ionisation steps. However, extension of this method to more than two ionisation steps is algebraically complicated.

An alternative data analysis method is target factor analysis (TFA). TFA can be used to deduce the pKa values from multiwavelength absorption spectra recorded at different time points (different pH) during the titration. An absorbance data matrix $N_s$ (absorption spectra)$\times N_w$ (wavelength) is decomposed into a linear combination of principal components using principal component analysis (PCA—refs: D. Perez-Bendito, Analyst, Vol. 115, 689–698 (1990) and E. R. Malinowski, Factor Analysis in Chemistry, 2nd Ed. 1991, pub. Wiley, New York) and the components are identified into one by transformation of the mathematical solution using TFA based on a suggested reaction model (Malinowski, as above). A practical example of the use of TFA in the determination of pKas for drug compounds is given in Allen R. I. et.al. J. Pharm. & Biomed. Analysis, 1998, vol. 17, 699–712 and a comparison of the approach with the first derivative analysis discussed above may be found in Tam, K. I. & Tacacs-Novak, K., Pharm. Research, submitted.

The method of continuous titration permits the creation of a fast linear pH gradient over a wide pH range, with the use of appropriate buffers as described below. This in turn allows the speedy determination of pKa values. The apparatus will generally be fitted with a pH meter in addition to a spectrophotometric detector, so that absorbance can be determined over time or against pH. However, if the speed of the pH gradient is fast, the pH electrode may not be able to respond quickly enough, giving erroneous readings. In this situation, the gradient can instead be calibrated using compounds of known pKa. Linear regression of the known pKas of standard compounds against the time of the peak maximum in the 1st derivative of the absorbance curve obtained for that compound in continuous titration, yields a calibration curve which can be used to determine the pKa of unknown compounds without pH measurement. The "time to peak maximum" of a test compound run through the same gradient is determined and the pKa is read off from the calibration curve. This "time to peak maximum" may be measured from the start of the apparatus cycle or from the start of the gradient, as convenient, the important criterion being that a consistent start time is used for all standard and test compounds run on the same gradient. Although calibration of the gradient is being used instead of direct pH measurement, the pH electrode may be kept in place as a diagnostic tool, e.g. to check correct instrumental operation, such as whether the pH gradient remains linear.

The present invention is particularly advantageous in the analysis of poorly soluble compounds, as only very small concentrations and volumes of solutions are required i.e. 100s down to 10s of micrograms per milliliter, and 100s of microliters, rather than 100s of milliliters for traditional methods. Also, the use of highly sensitive detectors combined with high data sampling rates allows the introduction of noise-reduction techniques and means that much less concentrated test solutions may be used. Furthermore, it is not necessary to know the concentration of the test compound, because the output can be presented graphically and the changes in e.g. absorbance are plotted rather than absolute values, graphical shape changes showing the changing ionisation state, phase or other changes in the test compound. It is sufficient that the concentration is such that the chromophore is detectable by the spectrophotometer.

In recent times the analytical chemist has been dealing with compounds produced in combinatorial chemical libraries which has led to the problems of increasing numbers of compounds to be tested, presented in decreasing quantities. As discussed above, the present invention provides methods and apparatus which will assist in overcoming these problems. There may also be problems in relation to sample purity when compounds are synthesised as part of a library, and the level of automation achievable by the use of continuous titration methodology as described herein may provide a means for overcoming those problems also. For example there is scope for "chaining" an HPLC chromatographic separation and continuous titration, so that samples purified on an HPLC instrument are collected in the vials of an autosampler for direct injection into the test mixture stream of a continuous titration apparatus as described herein. There would be no need for an operator to intervene. Furthermore, if the cycle times of the HPLC instrument and the continuous titration apparatus are coincident, then there is scope for a direct peak-divert of the purified library compounds into the test mixture stream of the continuous titration apparatus.

Particular embodiments of the present invention are described below, by way of example only, with reference to the accompanying drawings in which:

FIG. 12 shows a standards (calibration) curve derived from titration data obtained in accordance with the invention for compounds of known pKa;

EXAMPLES

Example 1

A. Apparatus of FIGS. 1 and 2

In a first embodiment, the apparatus was assembled from equipment already available in the laboratory, and consisted of the following units:
  Gilson Aspec XL autosampler;
  Hewlett Packard 1050 quaternary HPLC pump;
  Kontron 440 diode array detector (DAD) spectrophotometric detector;
  66 MHz 486 PC computer with Strawberry Tree Data acquisition card;

Dynares 8 Ultra (+71-TC) terminal panel;
Dasylab software is used for data capture;
PEEK tubing (1/16" outside diameter (OD)).

Diagrammatic representations of two arrangements of the apparatus can be seen in FIGS. 1 and 2 and are described further below along with the plumbing connections between the various units in the FIG. 2 arrangement (shown in FIG. 4) and the electrical connections thereof (in FIG. 5).

Figure 1:
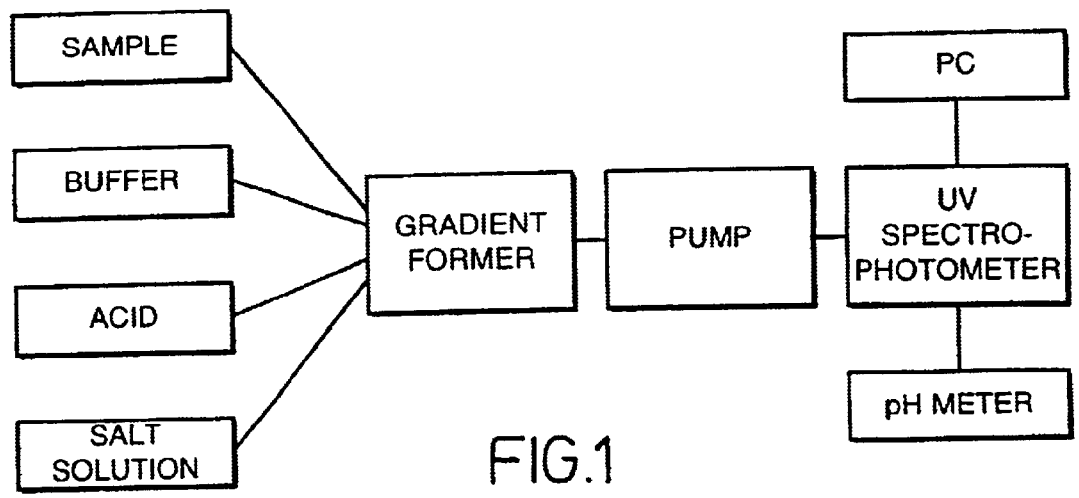
FIG. 1 is a diagrammatic representation of apparatus according to a first embodiment of the invention.

Improvements to Buffering System:

The system initially developed used four solutions mixed into a linear gradient (FIG. 1). The sample at constant % volume was titrated with acid (as in FIG. 1) or base and the % volume of salt solution was decreased as the acid or base increased, to maintain ionic strength within acceptable limits. The system was buffered by a constant % volume of buffer solution. Refinement of the buffering system has allowed this to be reduced to three components; a sample solution, the amount of which is not varied over the time that the gradient is run, and two linearising buffer solutions, one acidic and one basic, which are varied linearly over time in inverse proportion to one another. See FIG. 2.

Figure 2:
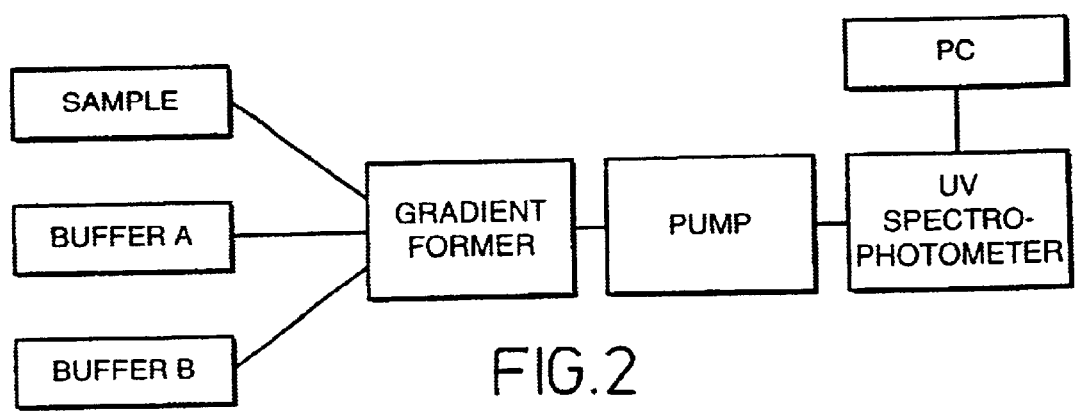
FIG. 2 is a diagrammatic representation of apparatus according to a second embodiment of the invention.
Figure 3:
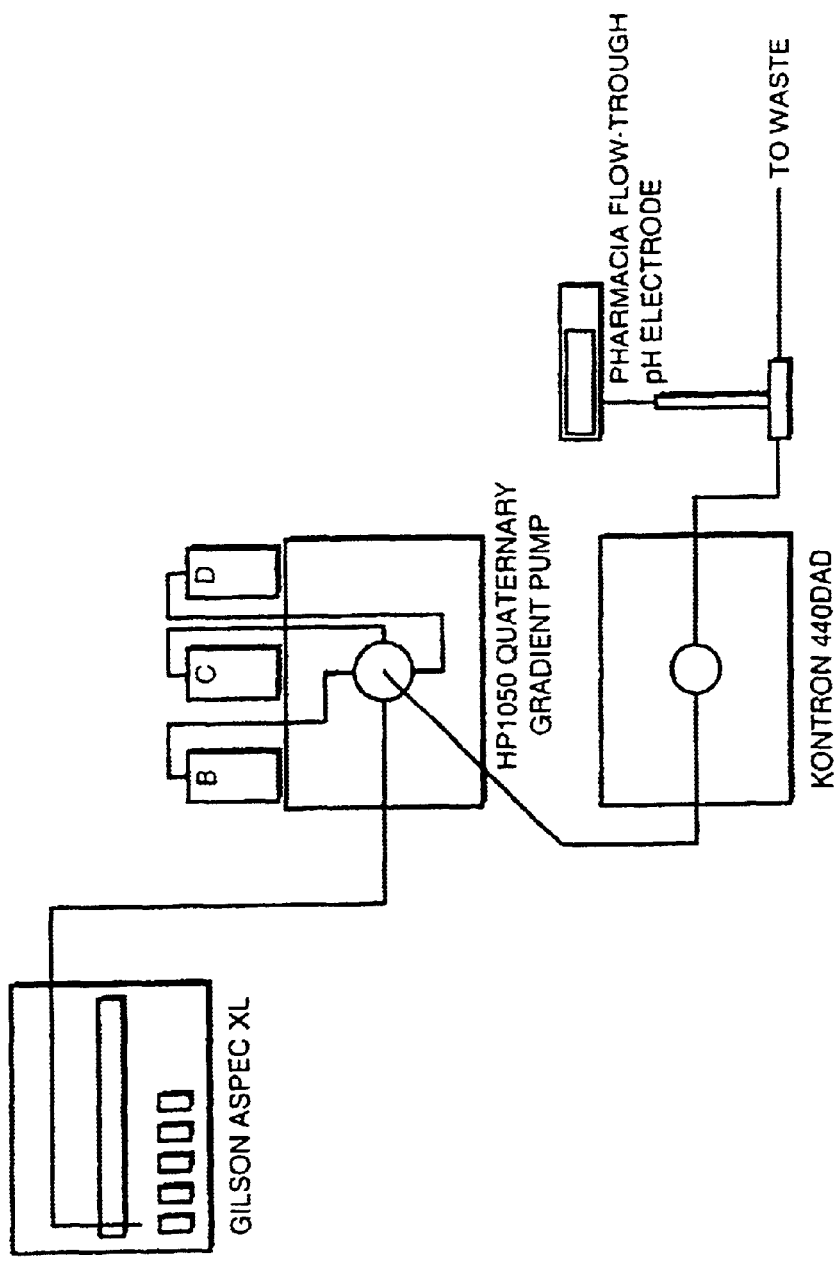
FIG. 3 is a diagrammatic representation of the plumbing connections of the apparatus of FIG. 2.

Operation of the Apparatus of FIG. 2:

During the running of the gradient, the sample containing the test compound is drawn at a constant rate from the autosampler into channel A of the HP1050 pump. At the same time, varying amounts of the other components are drawn into the pump. Universal buffer component B (basic component, see further below) is drawn into channel B from a reservoir. Similarly universal buffer compound A (acidic component) is drawn into channel C. One of the buffer components rises from zero or a low % volume of the test mixture at the start of the gradient to e.g. 80% or more of the mixture at the end. The other buffer falls from e.g. 80% or more of the mixture to zero or a low final concentration.

For a gradient of increasing pH, the proportion of buffer B will rise over the time of the gradient whilst the proportion of buffer A will fall. The remainder of the mixture is test compound solution (channel A), optionally with other components as necessary (e.g. water, surfactant micelles, reactant(s)) which may be supplied via channel D of the HPLC pump.

The mixed components pass from the outlet of the HPLC pump to the Spectrophotometer (Kontron 440DAD) and then to waste, optionally via a pH meter which may be used to monitor the correct operation of the system, e.g. to check the linearity of the pH gradient formed.

Tubing may suitably be 1/16" OD PEEK or stainless steel tubing.

When a number of samples are to be tested, the apparatus can be set to run through a repeating cycle during which there may be four distinct phases: 1) The buffers and any other components are pumped through the HPLC pump at constant rates in fixed ratios to give a stable starting point for the gradient. 2) The gradient is run by varying the ratios of the buffer components. 3) The final conditions of the gradient may be maintained for a short period before 4) the system recycles (which may include flushing with water of other suitable solvent at the end of the cycle), in preparation for the drawing up of the next sample.

Figure 4:
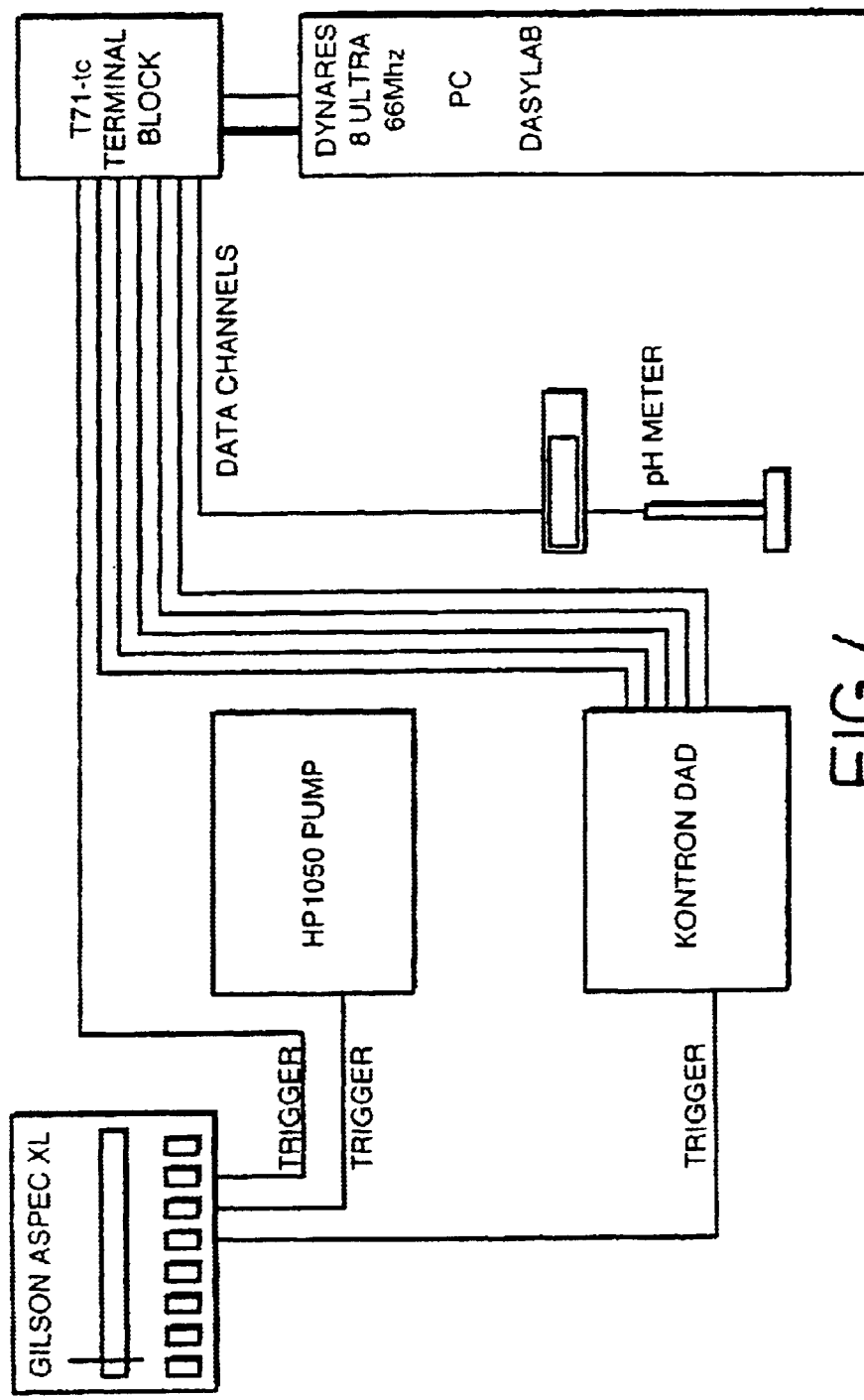
FIG. 4 is a diagrammatic representation of the electrical connections of the apparatus of FIG. 2.
Figure 5:
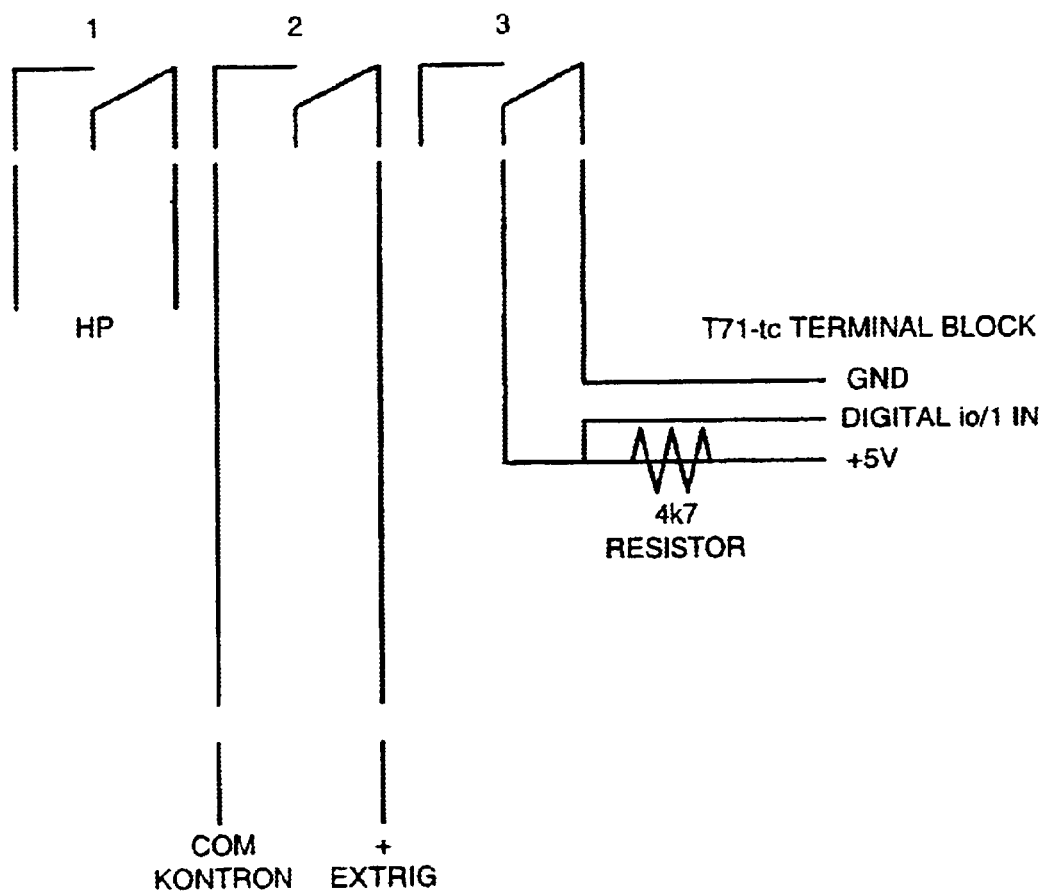
FIG. 5 is a diagrammatic representation of the electrical trigger events controlling the apparatus of FIG. 2.
Figure 6:
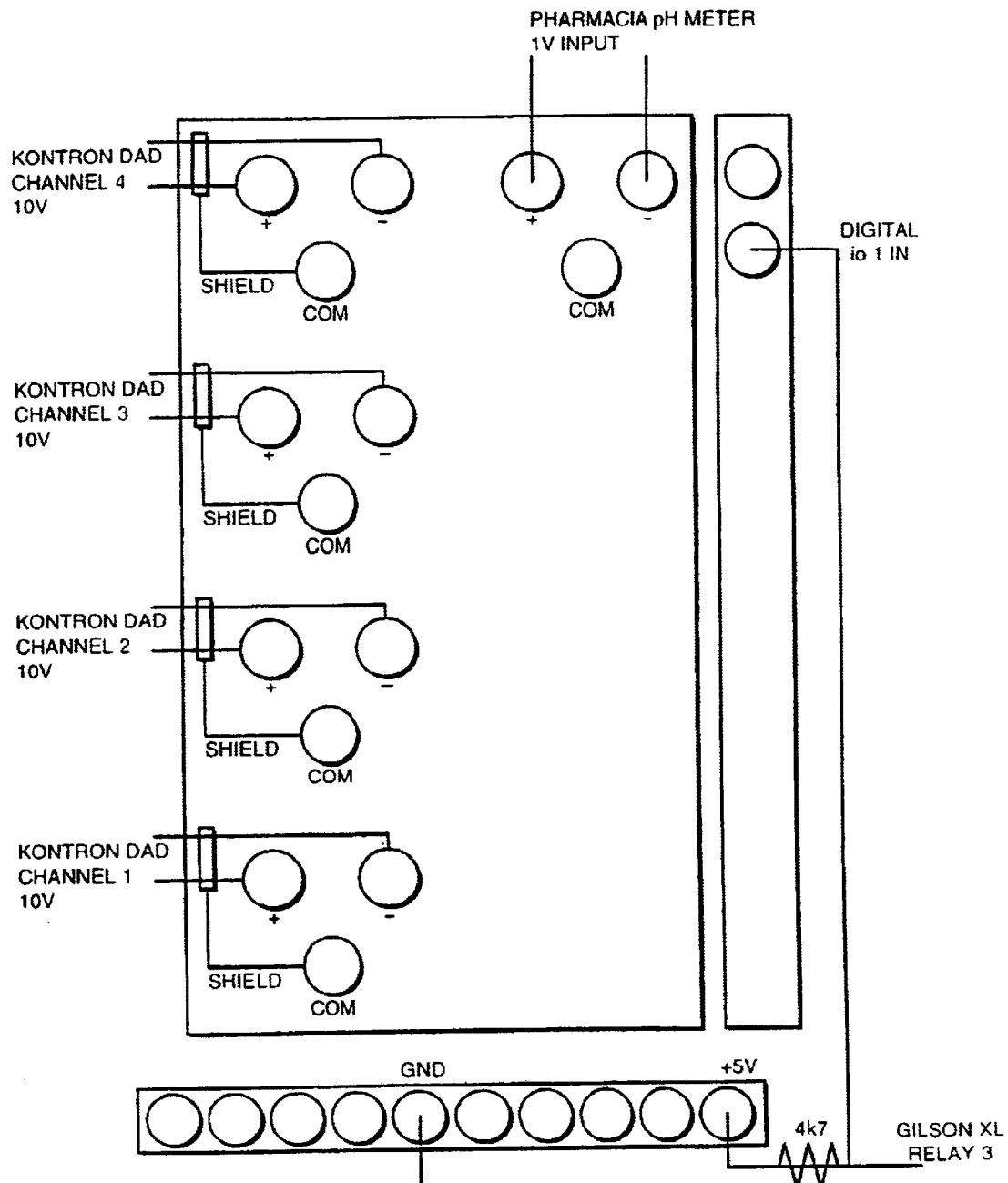
FIG. 6 is a detailed diagram showing the connections within the terminal block of the apparatus of FIG. 2.

Electrical Connections for the Apparatus of FIG. 2:

As can be seen from the outline of the electrical connections depicted in FIG. 4, analogue data from the spectrophotometer and pH meter are fed to the terminal block and thence to the PC for capture and analysis by Dasylab software. Any other software capable of capturing and manipulating analogue data would be suitable. This embodiment is limited to four analogue outputs from the spectrophotometer, the four data channels from the spectrophotometer are connected to shielded inputs 1 to 4 on the terminal block and the analogue signal from the pH meter is connected to terminal 5. Shielding of the cables reduces interference from high frequency instrumental noise. The connections within the terminal block are shown in more detail in FIG. 6.

As can be seen from FIG. 4, the autosampler is connected to the pump, spectrophotometer and terminal block. These contacts are digital signals which specify the start and finish of the experimental cycle, these contact closure events are driven by the autosampler. The signals to the pump and spectrophotometer are contact closures, the signal to the terminal block is a contact opening. This is shown in more detail in FIG. 5.

B. Further Embodiments

Figure 7:
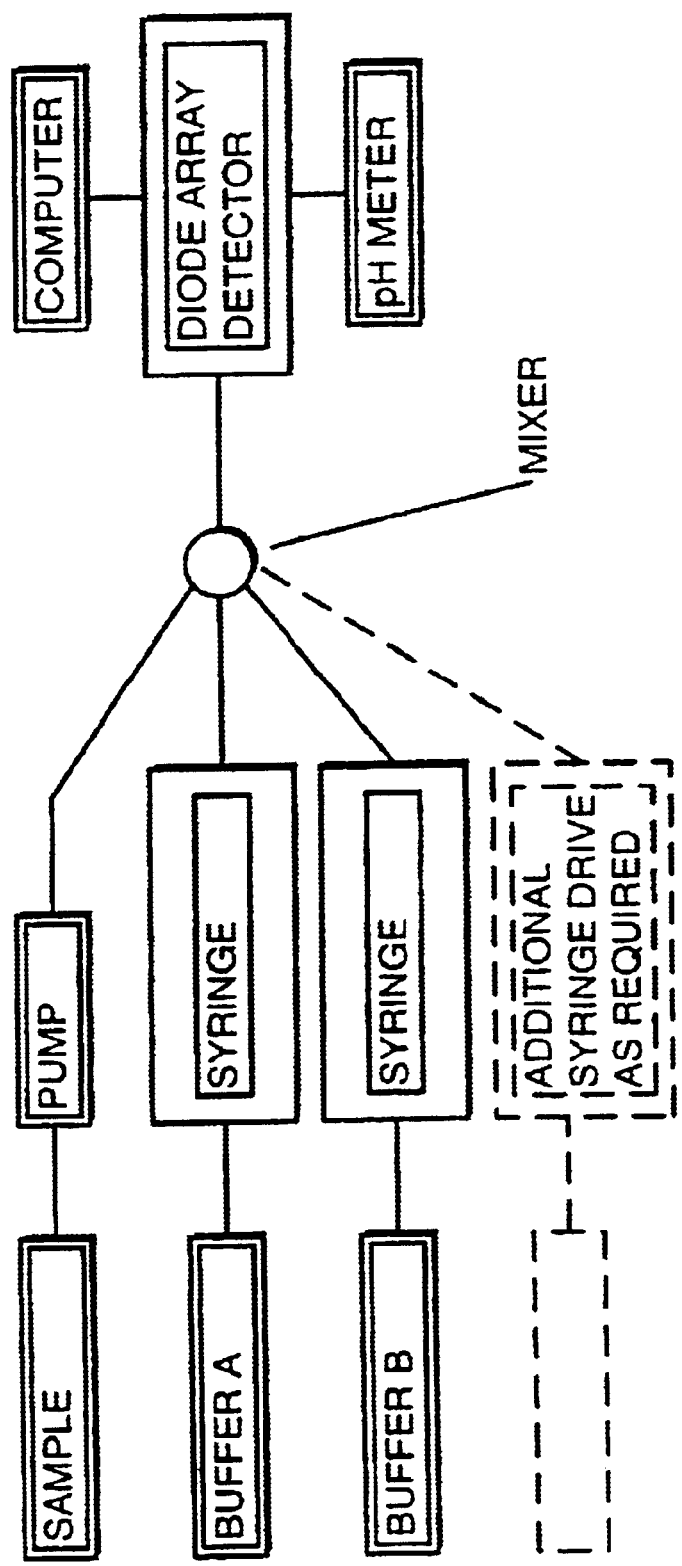
FIG. 7 is a diagrammatic representation of apparatus according to a third embodiment of the invention.

FIG. 7 shows a similar apparatus arrangement to that of FIG. 2, but the buffer components are introduced into the mixer from automatic syringes rather than being drawn up by the mixer pump from a reservoir. Any extra components such as micelle suspension for a partitioning experiment may also be introduced by syringe as may the test samples, if desired, although if multiple samples are to be tested the use of an autosampler instead of a pump or a syringe provides a convenient means of automation.

Figure 8:
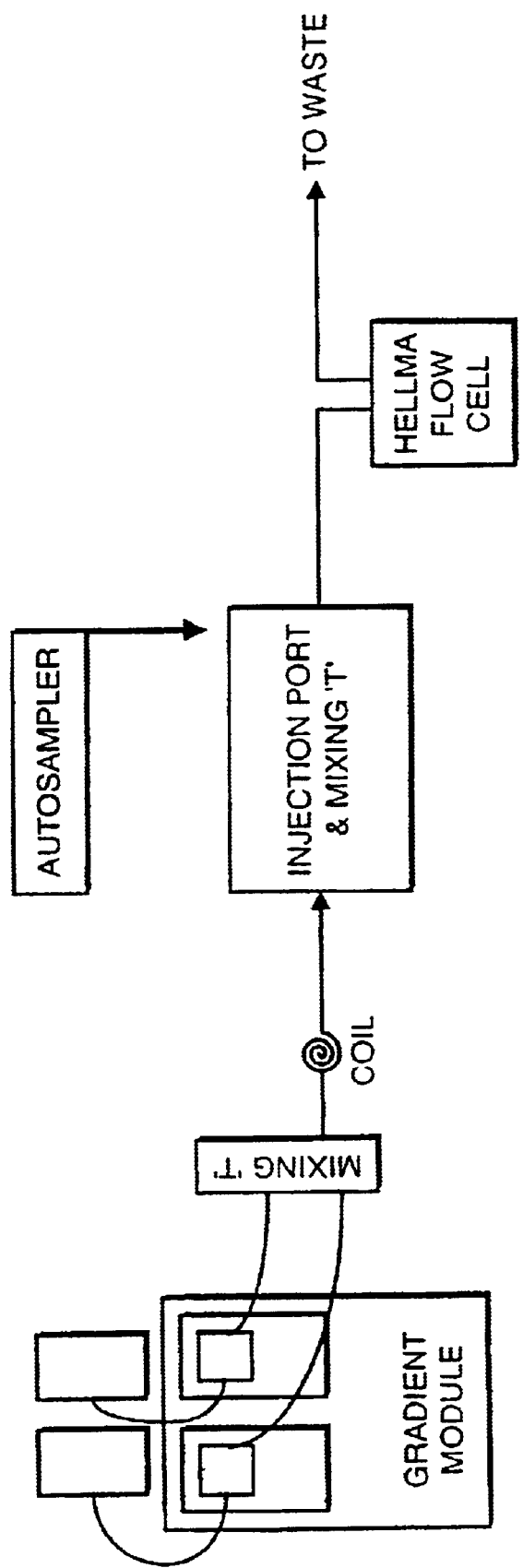
FIG. 8 is a diagrammatic representation of apparatus according to a fourth embodiment of the invention.
Figure 9:
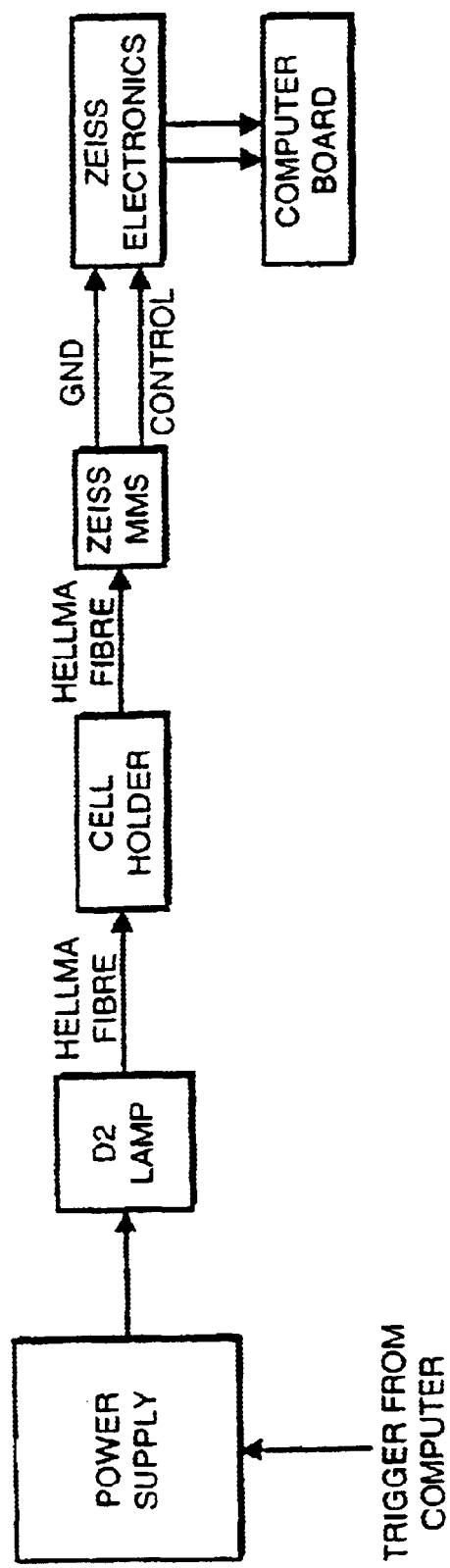
FIG. 9 is a diagrammatic representation of the detector connections of the apparatus of FIG. 8.

FIGS. 8 and 9 show another apparatus embodiment which uses automatic syringes for delivery of the gradient-forming components.

This apparatus uses the following units:
Sirius Gradient System (Sirius Analytical Instruments Ltd.)
Mixing T (Thames Restek)
Compact Ultra-micro flow-cell (Hellma—ref: 178.713)
FEP Tubing, OD 1.6 mm, ID 0.8 mm
MSP9000/XL3000/injection port (Cavro)
Pulsed lamp power supply (Cathodeon—C720)
Deuterium lamp, 210 nm-700 nm (Cathodeon—J27)
Remote cell holder (Hellma—664.000)
UV/VIS fibre cables with lenses (Hellma—041.002 UV/VIS)
MMS Spectrophotometer, 256 diode array (Zeiss—224000–9001.000)
MMS 12-bit adapter electronics (Zeiss—792200–9009.000)
Computerboards 12-bit CIO-DAS 16jr (Talisman)

As can be seen in FIG. 8, the two flow streams from the syringe dispensers are mixed using a mixing T which has a total volume of 4 $\mu$l. The flow stream then passes through a coil to aid mixing and then on to the injection port, located on the autosampler. The autosampler can inject samples in to the flow stream at this point. From the injection site, the stream flows on to the spectrophotometer's remote flow cell and then out to waste.

In FIG. 9 can be seen the electrical and fiberoptic connections associated with the detector used with the apparatus of FIG. 8. The deuterium lamp is controlled via a transistor-transistor logic (TTL) signal which in-turn controls the power circuitry in the power supply. The deuterium lamp should be warmed up before commencing experiments. This is typically for about half an hour. The TTL signal is controlled via the computer, allowing the lamp to be turned off and on automatically. A transmission fibre optic runs from the lamp to transmit the light from the lamp to the cell holder. The cell holder is used to position the flow cell in-line with the light path. The position of the receiving fibre can be adjusted within the cell holder, and then fixed in place using a locking screw. This fibre then connects to the MMS spectrophotometer. The MMS 12-bit adapter electronics perform the data capture from the spectrophotometer, under the control of signals from the CIO-DAS 16jr computer board.

Control:

The main control program has been programmed as a LabView Virtual Instrument. It is used to control the main peripherals:

The lamp for the spectrophotometer (i.e. turn on/off).

The gradient module (sends trigger signal, and configures)

The autosampler (sends the correct control strings)

The spectrophotometer (provides clock pulses and receives triggers)

The main control program initially configures all the external peripherals and brings them into a ready state. The user can select a filename for where they want all the data to be saved from the run about to commence. Once this is completed, the instrument enters a holding state where the user can either run experiments individually totally under their control, or they can set a programmed number of samples to run continuously until completion.

The Sirius Gradient System includes an 80C552 microprocessor based control board, two Sirius syringe dispensers, a Datavision LCD and a keypad. The LCD and keypad provides a simple user interface that allows a user to programme gradient control variables for the flow stream. The gradient system can also be controlled via an RS-232 interface. The gradient module has an embedded software program that allows the user to set up experimental parameters for generating the gradient. The set up parameters for the gradient control are:

The total flow rate in ml/min.

The gradient reset time in seconds (e.g. if the gradient goes from low to high, the gradient needs to be reset back to low before the next sample is injected).

The total gradient time in seconds.

The post gradient time in seconds (this pushes the end of the gradient through to the flow cell).

These parameters can also be initialised, via a serial port, from a controlling computer. Both syringes can be controlled simultaneously. Once the gradient module is put in to the READY state, the gradient control protocol can be started using an external trigger signal, supplied automatically from the main control computer. When this signal is detected the gradient module begins its operational run, at the end of which it automatically reloads, then waits for the next trigger signal for the start of the next experiment.

Figure 10:
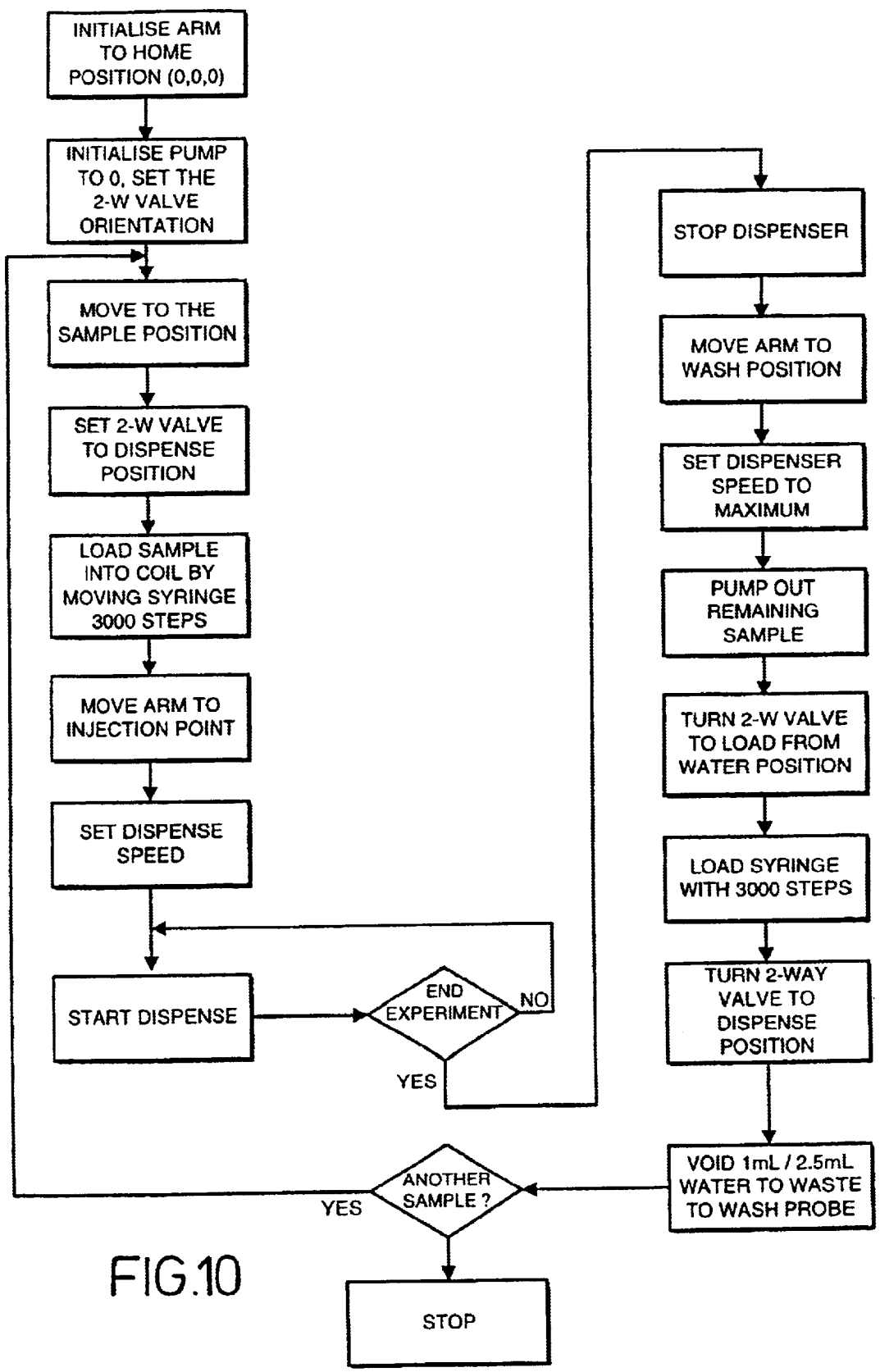
FIG. 10 is a flow-chart depicting the control sequence for the autosampler in the apparatus of FIG. 8.
Figure 11:
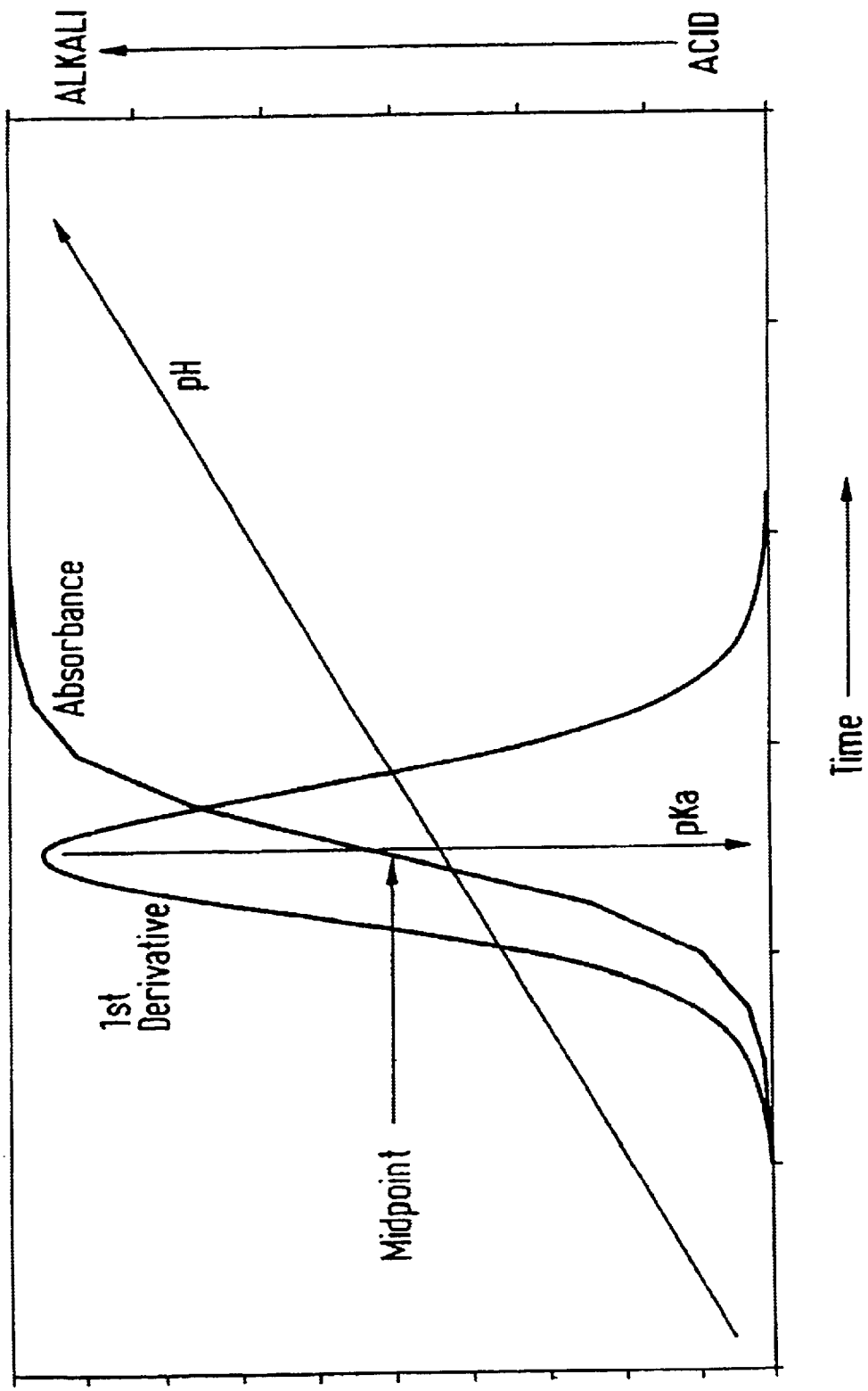
FIG. 11 is a diagrammatic representation of the relationship between pKa, absorbance and 1st derivative of absorbance for a species having a single ionisable group in which the ionised and unionised forms have different absorbance profiles.

When a sample run begins, the autosampler loads the sample into a coil. FIG. 10 shows a flow chart of the autosampler control. The arm then moves to the injection point. A trigger is sent to the gradient module to start the gradient flow and also to the deuterium lamp. At the predefined time, data collection begins at 0.5 second intervals. The sample is injected into the gradient stream. The instrument actually captures six scans from the spectrophotometer, averages the last five scans and uses this average as the stored scan. This is done by calling a CIN (Code interface node) which liaises with the CIO-DAS 16/Jr board, collects the 256-absorbance spectra and returns this data array to the VI which saves it on disk in the specified file.

Data Capture and Data Processing:

The data capture routine has been simplified by implementing hardware to control and time the data acquisition of the signal from the diode array. The hardware is encompassed in the Zeiss electronics, along with the signal conditioning electronics. The data capture routine is required to send a trigger signal to indicate that a scan is required. The Zeiss electronics controls the diode array and the data capture board. The Zeiss electronics also conditions the signal from 0V to +2.5V, making full use of the resolution of the Analogue-to-digital converter (ADC).

To increase the signal to noise ratio, a dark scan (lamp off) is made, and this result is subtracted from all other scans (lamp on). For each scan, the signal is sampled six times, the first scan is discarded and the remaining five scans are then averaged. This averaged scan is then saved to disk. This takes about 300 ms. Scans are recorded at 500 ms intervals. The resultant data file contains 256 wavelengths of data for each sample.

The data file, containing 480 data points per wavelength, is converted into a format suitable for data processing by either first derivative or TFA analysis. Diode array data is in terms of "energy counts" which need to be converted to Absorbance data using the equation:

$$A = \log 10((I(I(\text{ref})-I(\text{dark}))/(I(\text{sample})-I(\text{dark})))$$

where:

$I(\text{sample})$ is the intensity or energy count of the gradient with sample for a particular channel or wavelength;

$I(\text{dark})$ is the dark current; and $I(\text{ref})$ is the initial reference count (buffer B plus sample).

The convert program allows the user to specify which wavelengths need to be extracted for use in the data processing algorithm, and formats the resultant data file. However, in order to use TFA, the 1st derivative program must be run first to calculate the pH gradient. The pH gradient is calculated by using data from compounds that have well defined pKas, and have thus been termed 'standards'. This then provides the pH scale required for the TFA algorithm.

Before any samples can be run through the system, a blank sample (just water or appropriate solvent) and calibration standards must be run. The blank sample provides a blank profile, providing absorption information due to the gradient and the water. This must be subtracted from all the standard/sample runs. This then provides an absorption profile purely due to the standard/sample. To obtain the absorption peaks from the data, the data processing algorithm uses a linear fit algorithm to smooth the data and then performs the derivative upon the slope of the linear fit. The user is able to specify the number of points over which the fit is applied (it must be an odd number of points). The data processing algorithm is applied to each point in the data file. Once this has been completed, peaks need to be found. This is done by dividing the data into cells (user specified size), and in each cell, searching for peaks that fit the criteria for a minimum or maximum peak.

Example 2

A. Determination of pKa—Apparatus of FIG. 2

FIG. 2 shows a diagrammatic representation of apparatus used to form a buffered linear pH gradient. The following pKa determination experiment was performed on this apparatus.

A linear pH gradient was created by mixing a sample solution, the amount of which is not varied over the time that the gradient is run, and two buffer solutions, one acidic and one basic, which are varied linearly over time in inverse proportion to one another. The two buffers have a common component to which an acidic component is added to form buffer A and a basic component is added to form buffer B. The buffers were made up as follows:

Solution C: Common Component (1 liter)

Into 1 liter of water:

| | | | |
|---|---|---|---|
| Boric Acid (FLUKA 15660) | 24.732 g | (Mw: 61.83) = | 0.4M |
| TRIS (FLUKA 93350) (hydroxymethyl)-aminomethane) | 48.456 g | (Mw: 121.4) = | 0.4M |
| Butylamine (FLUKA 19480) | 29.256 g | (39.696 cm$^3$) = (Mw: 73.14, density 0.737) | 0.4M |

Buffer A—1 liter

Into 500 cm$^3$ Solution C:

| | | |
|---|---|---|
| $KH_2PO_4$ (BDH ANALAR 10203) | 27.218 g | (Mw: 136.09) |
| Citric Acid Monohydrate | 42.028 g | (Mw: 210.14) |
| HCl | 350 cm$^3$ | (1 m solution) | made up to 1000 cm$^3$ total volume with $H_2O$ to give:

| | |
|---|---|
| $KH_2PO_4$ | 0.2M |
| Citric Acid Monohydrate | 0.2M |
| HCl | 0.35M |
| pH = | ~2.8 |

Buffer B—1 liter

Into 500 cm$^3$ Solution C;

| | | |
|---|---|---|
| $K_2HPO_4$ (FLUKA 60356) | 34.836 g | (Mw: 174.18) |
| $K_3$Citrate (Monohydrate) (FLUKA 60153) | 64.884 g | (Mw: 324.42) |
| KOH (ALDRICH 31,936-8) | 400 cm$^3$ (0.5 M) | | made up to 1000 cm$^3$ total volume with $H_2O$ to give:

| | |
|---|---|
| $K_2KPO_4$ | 0.2M |
| $K_3$Citrate | 0.2M |
| KOH | 0.2M |
| pH = | ~11.58 |

Buffer component A (acidic) and B (basic) need to be diluted 1:10 before use in an HPLC gradient. This gives pH values of the diluted buffers as follows:

Acidic (Buffer A)=3.01

Basic (Buffer B)=11.19

The linearity of this buffer system was tested stepwise by using an HP1050 HPLC pump to mix the buffers at a flow rate of 5 cm$^3$ min$^{-1}$, with the pH being monitored with a flow-through Pharmacia pH electrode. The relative amounts of buffer A and buffer B were kept constant until the pH reading was stable then stepped to their next values and held again until a stable reading was achieved before being stepped once more. This was repeated until the gradient was completed.

The results are set out below and represented graphically in FIG. 18

| % Buffer A | % Buffer B | pH |
|---|---|---|
| 100 | 0 | 2.91 |
| 90 | 10 | 3.9 |
| 80 | 20 | 4.71 |
| 70 | 30 | 5.45 |
| 60 | 40 | 6.2 |
| 50 | 50 | 6.98 |
| 40 | 60 | 7.77 |
| 30 | 70 | 8.57 |
| 20 | 80 | 9.46 |
| 10 | 90 | 10.39 |
| 0 | 100 | 11 |

Figure 18:
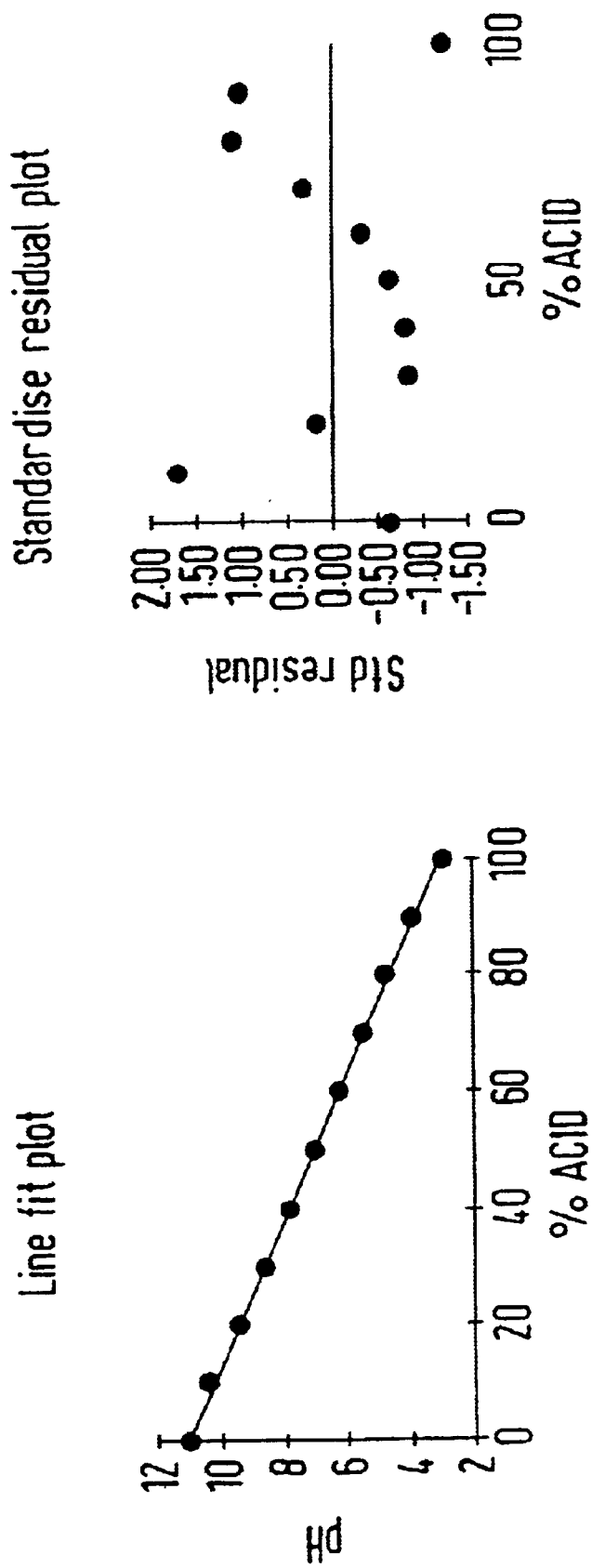
FIG. 18 is a plot of pH against % acid for the linear gradient on which the standards (calibration) curve of FIG. 12 was produced.

FIG. 18 shows that the pH gradient is essentially linear from pH 3 to 11. Compounds of known pKa were run in a continuous (rather than stepped) gradient on the apparatus of FIG. 2, in which the amount of buffer A ran from 80% to 0% and of buffer B from 0% to 80% of the test mixture over 4 minutes. The sample solution was kept constant at 20%. The HP1050 pump was used again with buffer B introduced via channel B and buffer A via channel C. The flow rate of the test mixture stream from the mixer to the detector was 1 cm$^3$ min$^{-1}$.

The absorbance changes at 240 nm, 265 nm, 290 nm and 315 nm were recorded and the peak maxima of the 1st derivative plots determined. A calibration curve (FIG. 12) was created from the time to peak maxima and the known pKa values (determined by conventional titration) of the standards. Compounds of known pKa were also determined as test solutes.

The calibration results are set out below: Time to peak maximum is from the start of the instrument cycle (when the autosampler first goes into a new sample container).

Standards

| | Known pKa* | Time to peak maximum | | |
|---|---|---|---|---|
| Benzoic acid | 3.96 | 217.3 | | |
| Phenol | 9.766 | 444.8 | | |
| phthalate 1 † | 4.82 | 251.8 | | |
| 4-NO$_2$phenol | 6.89 | 334.7 | Intercept | −1.5717 |
| Benzoic acid | 3.96 | 216.3 | Slope | 0.0254 |
| Phenol | 9.766 | 445 | | |
| phthalate 1 | 4.82 | 249.8 | R2 = | 0.9998 |
| 4-NO$_2$phenol | 6.89 | 334.9 | | |
| Benzoic acid | 3.96 | 216.5 | | |
| Phenol | 9.766 | 444.3 | | |
| phthalate 1 | 4.82 | 251.5 | | |
| 4-NO$_2$phenol | 6.89 | 334.7 | | |

† the more alkaline of the two potassium hydrogen phthalate pKa values.
*determined by potentiometric titration on Sirius PCA 101 instrument in 0.15 KCl.

Results for the test solutes and residuals are set out below:

| Sample | Known pKa* | Time to Peak Maximum | pKa Derived | Residual |
|---|---|---|---|---|
| 3-Cl phenol | 8.81 | 407.5 | 8.79 | 0.02 |
| 4-Cl phenol | 9.14 | 421.2 | 9.14 | 0.00 |
| 2-Cl phenol | 8.24 | 382.8 | 8.16 | 0.08 |
| 4-CN phenol | 7.7 | 360 | 7.58 | 0.12 |
| 3-Cl phenol | 8.81 | 406.8 | 8.78 | 0.03 |
| 4-Cl phenol | 9.14 | 420.8 | 9.13 | 0.01 |
| 2-Cl phenol | 8.24 | 382.3 | 8.15 | 0.09 |

-continued

| Sample | Known pKa* | Time to Peak Maximum | pKa Derived | Residual |
|---|---|---|---|---|
| 4-CN phenol | 7.7 | 361.3 | 7.62 | 0.08 |
| 3-Cl phenol | 8.81 | 407.3 | 8.79 | 0.02 |
| 4-Cl phenol | 9.14 | 421 | 9.14 | 0.00 |
| 2-Cl phenol | 8.24 | 382.3 | 8.15 | 0.09 |
| 4-CN phenol | 7.7 | 360 | 7.58 | 0.12 |

*determined by potentiometric titration on Sirius PCA 101 instrument in 0.15 KCl.

The derived pKa values taken from the standards calibration curve are very close to those expected.

Figure 13:
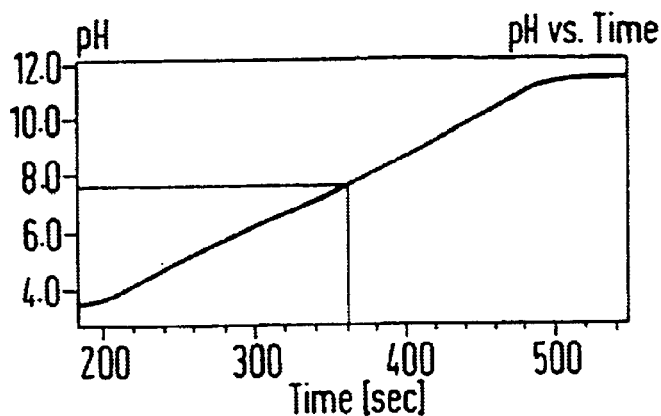
FIG. 13 is a plot of pH against time for the linear gradient.
Figure 14:
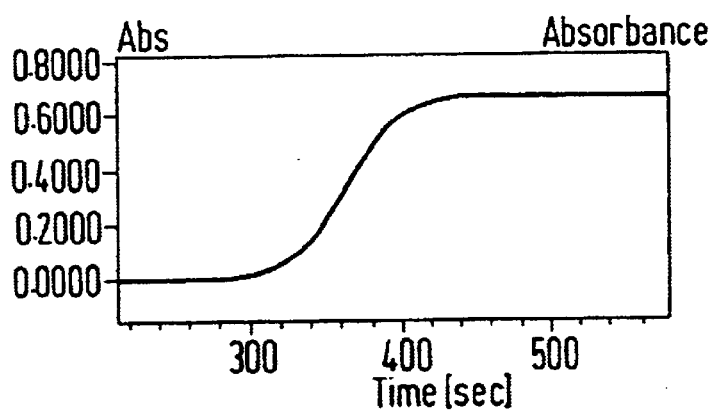
FIG. 14 is an absorbance curve for 4-CN phenol run on the gradient of FIG. 13.
Figure 15:
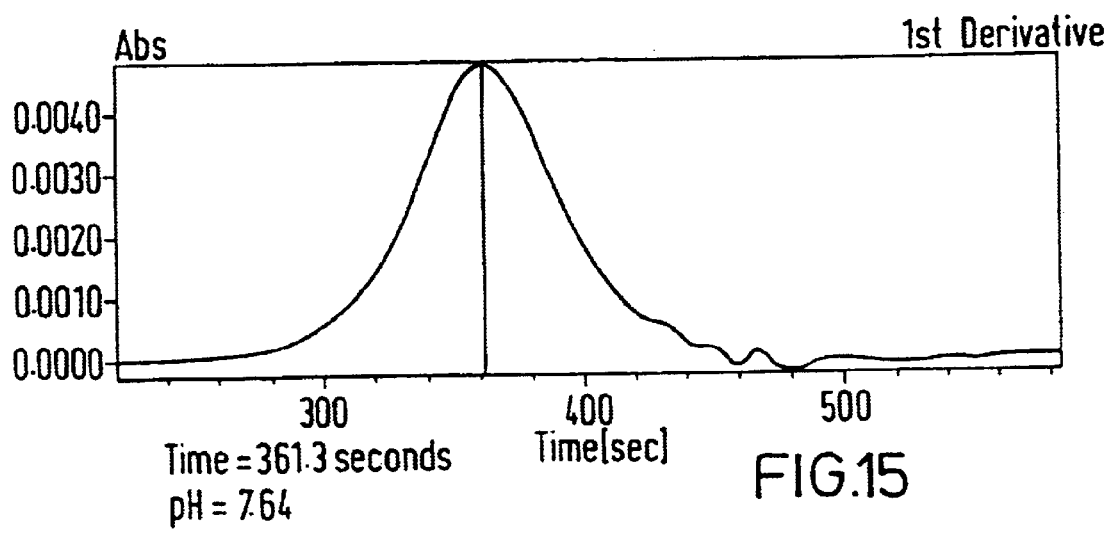
FIG. 15 is a plot of the first derivative of the absorbance readings plotted in FIG. 14.

FIGS. 13, 14 and 15 show the calibration curve (FIG. 13) with the absorbance curve at 290 nm (FIG. 14) and the 1st derivative plot (FIG. 15) for 4-CN phenol run on the above gradient. When the pKa value corresponding to the time of the peak maximum (361 seconds) is read from the calibration curve for this pH gradient, the pKa derived is 7.64. The expected result is 7.7 (derived from traditional stepwise titration using the Sirius PCA101 instrument).

The method could be further enhanced by incorporation of the calibration curve into the data handling routines, for example the computer which stores the absorbance readings generated by the detector may be programmed to find the first derivatives of these readings, determine the time of the peak reading and, for example using a look-up table derived from the calibration curve absorbance readings, produce an output reading giving the pKa of the sample. The pKa reading would then be the only output—no calculations would be required on the part of the operator.

B. Determination of pKa—Apparatus of FIG. 8

Gradient:

The buffer recipes have been further optimised to improve gradient linearity while maintaining physiological ionic strength without significantly reducing the buffer capacity. The Components were also chosen with minimal UV/visible absorption characteristics. Recipes are shown below and compared to the recipe of Example 2A above:

Component A (acidic buffer):

| | Example 2A recipe | Optimised recipe |
|---|---|---|
| TRIS (M) | 0.020 | 0.01237 |
| Boric acid (M) | 0.020 | 0.01397 |
| Butylamine (M) | 0.020 | 0.01514 |
| Citric acid (M) | 0.020 | 0.01391 |
| KH$_2$PO$_4$ (M) | 0.020 | 0.01264 |
| HCl (M) | 0.035 | 0.03 |

Component B (basic buffer):

| | Example 2A recipe | Optimised recipe |
|---|---|---|
| TRIS (M) | 0.020 | 0.01237 |
| Boric acid (M) | 0.020 | 0.01397 |
| Butylamine (M) | 0.020 | 0.01514 |
| K$_3$ Citrate (M) | 0.020 | 0.01391 |
| K$_2$HPO$_4$ (M) | 0.020 | 0.01264 |
| KOH (M) | 0.020 | 0.02 |

Gradient composition:

| | Example 2A recipe | Optimised recipe |
|---|---|---|
| Supporting electrolyte (KCl, M) | 0.00 | 0.010 |
| Mean ionic strength (M) | 0.197 ± 0.049 | 0.150 ± 0.034 |
| Linear pH range | 3–11 | 3–11 |
| Correlation coefficient (R$^2$) | −0.999801 | −0.999870 |
| Slope | −8.296101 | −9.535502 |
| Intercept | 11.148199 | 11.820707 |
| Root-mean-square-deviation (RMSD) | 0.047062 | 0.037603 |
| mean buffer capacity | 0.016 ± 0.002 | 0.011 ± 0.001 |

Method:

Initially, buffer component B is dispensed at a flow-rate of 1 ml/min and sample injected downstream (from the CAVRO autosampler) at a flow-rate of 0.25 ml/min to produce a total flow of 1.25 ml/min. Before each experiment a dark spectrum (lamp off) is recorded. After the flow has reached the Helima flow-cell (model 178.713, path length 10 mm, volume 8 μL) the deuterium lamp (Cathodeon) is switched on from the Cathodeon C720 deuterium pulsed lamp power supply and a reference energy spectrum recorded with sample and buffer B present. The gradient is started and run over a time period of 240 seconds during which the buffer components are varied linearly over time in inverse proportion to one another, starting with component B (basic buffer) and changing to component A (acidic buffer) at the end of the 240s time period. The total gradient flow-rate is maintained at 1 ml/min. After the gradient has finished, buffer A and sample are allowed to run through for a short period of time to push the end of the gradient through the flow-cell before switching back to buffer B, to restore the initial conditions ready for the next sample.

After the lamp has been switched on, spectra are recorded at 0.5 second intervals for the duration of the gradient using a Zeiss 256 wavelength photodiode array and 12-bit data capture electronics. Each spectrum consists of the average of five scans using an integration time of 50 milliseconds and records the energy count per diode channel minus the dark current.

Standards and Calibration:

Four standards with known (literature) pKas are run with every autosampler tray to establish the pH scale; benzoic acid (pKa 3.96), potassium hydrogen phthalate (pKa 4.87), p-nitrophenol (pKa 6.90) and phenol (pKa 9.72). Linear regression of the known pKas of the standard compounds against the time of the peak maximum in the 1st derivative of the absorbance curve for that compound yields a calibration curve that can be used to determine the pKa of the unknown compounds. Several Blanks (de-ionised water) are also run with each tray so that background subtraction of the absorbance profile of the buffer components can be applied.

Sample Preparation:

Typically, a 1–10 mg sample is weighed into a vial to which 1 ml methanol is dispensed, to aid sample dissolution, followed by 10 ml de-ionised water (>10$^{14}$ MΩ). The solutions are drawn into 5 ml disposable syringes and dispensed directly into test tubes through disposable nylon filters to remove undissolved solid. The test-tubes are transferred directly to the Cavro autosampler unit for sample analysis. The sample flow makes up 20% of the total flow so that typical sample concentrations at the flow-cell detector are $10^{-3}$–$10^{-5}$ M.

Data Processing:

The first stage is to establish the pH scale using the peak maximum time in the first derivative of the absorbance curve. Several wavelengths are used (benzoic acid—235 nm; KHP—278 nm; p-nitrophenol—321 nm; phenol—235 nm) and the energy spectra converted to absorbance:

$$A = \log 10((I(\text{ref}) - I(\text{dark}))/(I(\text{sample}) - I(\text{dark})))$$

where:

I(sample) is the intensity or energy count of the gradient with sample for a particular channel or wavelength;

I(dark) is the dark current; and

I(ref) is the initial reference count (buffer B plus sample).

Blanks are processed first and subtracted from all sample and standard spectra. Peak times of the standards are plotted against the known pKa values and the calibration history saved to file. For a given set of experimental conditions the calibration regression equation has been shown to be remarkably consistent for periods of weeks reducing the necessity of more than daily calibration.

Once the derivative method has established the pH at the start and end time of the gradient, sample data can be processed. Typically, up to twenty evenly spaced wavelengths are selected for sample analysis ranging from 210–350 nm and energy counts converted to absorbance as above. Internal referencing can also be applied by selecting a non-absorbing region of the spectrum (usually 420–440 nm) and establishing a baseline from a Blank to correct for any drift. Target Factor Analysis (TFA) is applied to determine the pKa values of samples. The first derivative method can also be applied to samples with non-overlapping pKa values.

The results of several autosampler runs on the FIG. 8 apparatus and using the optimised buffers, using both 1st derivative and TFA data processing methods, are given below for a selection of UV absorbing compounds, with a comparison with literature pKa values. The results show the accurate determination of pKas for a wide range of compounds, some multiple, very close pKas which have traditionally proven difficult to resolve. We have found that these can often be determined using continuous titration with the TFA data processing, and sometimes also using the 1st derivative data analysis method.

Calibration Curve: pH=–0.021×time+12.49 ($R^2$=0.9950)

|  | $pK_a$ |
| --- | --- |
| KHP | 4.878 |
| Phenol | 9.721 |
| Benzoic acid | 3.964 |
| p-nitrophenol | 6.869 |

Results: (see also FIG. 25)

| Sample | pKa (lit. data) | pKa (TFA) | pKa (1st Deriv.) |
| --- | --- | --- | --- |
| Benzoic acid | 3.98 ± 0.02[a] | 3.99 ± 0.04 | 3.75 ± 0.04 |
| Phenylacetic acid | 4.07[b] | 4.34 ± 0.01 | N.A.[d] |
| Trans-cinnamic acid | 4.20[b] | 4.15 ± 0.01 | 3.90 ± 0.17 |
| 4-Aminobenzoic acid | 2.46 ± 0.01[a] | 2.22 ± 0.05 | 2.45 ± 0.06 |
|  | 4.62 ± 0.01[a] | 4.79 ± 0.04 | 4.48 ± 0.08 |
| 3-Aminobenzoic acid | 3.15 ± 0.01[a] | 3.39 ± 0.08 | 2.95 ± 0.09 |
|  | 4.53 ± 0.01[a] | 4.73 ± 0.05 | 4.35 ± 0.13 |
| 2-Aminobenzoic acid | 2.15 ± 0.01[a] | 1.99 ± 0.09 | 2.28 ± 0.21 |
|  | 4.75 ± 0.01[a] | 4.75 ± 0.03 | 4.51 ± 0.09 |
| 4-Chlorophenol | 9.17[b] | 9.03 ± 0.03 | 9.16 ± 0.08 |
| 4-Hydroxybenzoic acid | 4.33 ± 0.01[a] | 4.22 ± 0.05 | 4.08 ± 0.12 |
|  | 8.97 ± 0.01[a] | 9.10 ± 0.02 | 9.13 ± 0.17 |
| Sotalol | 8.28 ± 0.01[a] | 7.96 ± 0.03 | 8.17 ± 0.12 |
|  | .72 ± 0.01[a] | N.A. | N.A. |
| Phenolphthalein | 8.83 ± 0.08[c] | 8.84 ± 0.05 | N.A. |
|  | 9.32 ± 0.10[c] | 9.32 ± 0.05 | 9.25 ± 0.10 |

[a] Measured pH-metrically at 25° C. and an ionic strength of 0.15 M
[b] Albert & Serjeant, 1984; corrected for an ionic strength of 0.15 M
[c] Mchedlovpetrosyan et al., J. Anal. Chem. USSR, 1984, 39, 1105; measured spectrophotometrically at 25° C. and an ionic strength of 0.2 M
[d] Not available Calibration Curve: pH=–0.022×time+12.66 ($R^2$=0.9955)

|  | $pK_a$ |
| --- | --- |
| KHP | 4.878 |
| Phenol | 9.721 |
| Benzioc acid | 3.964 |
| p-nitrophenol | 6.869 |

Results: (see also FIG. 26)

| Sample | pKa (lit. data) | pKa (TFA) | pKa (1st Deriv.) |
| --- | --- | --- | --- |
| 4-Chlorophenol | 9.17[a] | 9.04 ± 0.01 | 9.25 ± 0.07 |
| Sotalol | 8.28 ± 0.01[b] | 7.99 ± 0.03 | 8.12 ± 0.20 |
|  | 9.72 ± 0.01[b] | N.A.[c] | N.A. |
| Trans-styrylacetic acid |  | 4.57 ± 0.05 | N.A. |
| Pyridine | 5.23[a] | 5.27 ± 0.10 | 5.14 ± 0.22 |
| Benzylamine | 9.34[a] | 9.23 ± 0.10 | N.A. |
| Phenylethylamine | 9.83[a] | 9.64 ± 0.07 | N.A. |
| Tryptamine | 10.20[a] | 9.67 ± 0.03 | 10.05 ± 0.10 |
| 1-(3-Aminopropyl) imidazole |  | 5.73 ± 0.08 | 5.81 ± 0.40 |
|  |  | 9.28 ± 0.17 | N.A. |
| Quinine | 4.24 ± 0.09[b] | 4.30 ± 0.09 | 3.77 ± 0.28 |
|  | 8.55 ± 0.04[b] | 8.27 ± 0.10 | 8.35 ± 0.23 |
| Serotonin | 9.80[a] | N.A. | N.A. |
|  | 10.04[a] | 10.09 ± 0.03 | 10.03 ± 0.08 |

[a] Albert & Serjeant, 1984; corrected for an ionic strength of 0.15 M
[b] Measured pH-metrically at 25° C. and an ionic strength of 0.15 M
[c] Not available Similarly, 35 compounds were run on the FIG. 8 apparatus using the buffers set out in Experiment 2A. First derivative data processing was used. The results were compared to the literature pKas for the compounds. Compounds with a wide range of pKas were chosen to demonstrate the accuracy of the continuous titration method across over a large pH range. The results are depicted graphically in FIG. 27.

Figure 25:
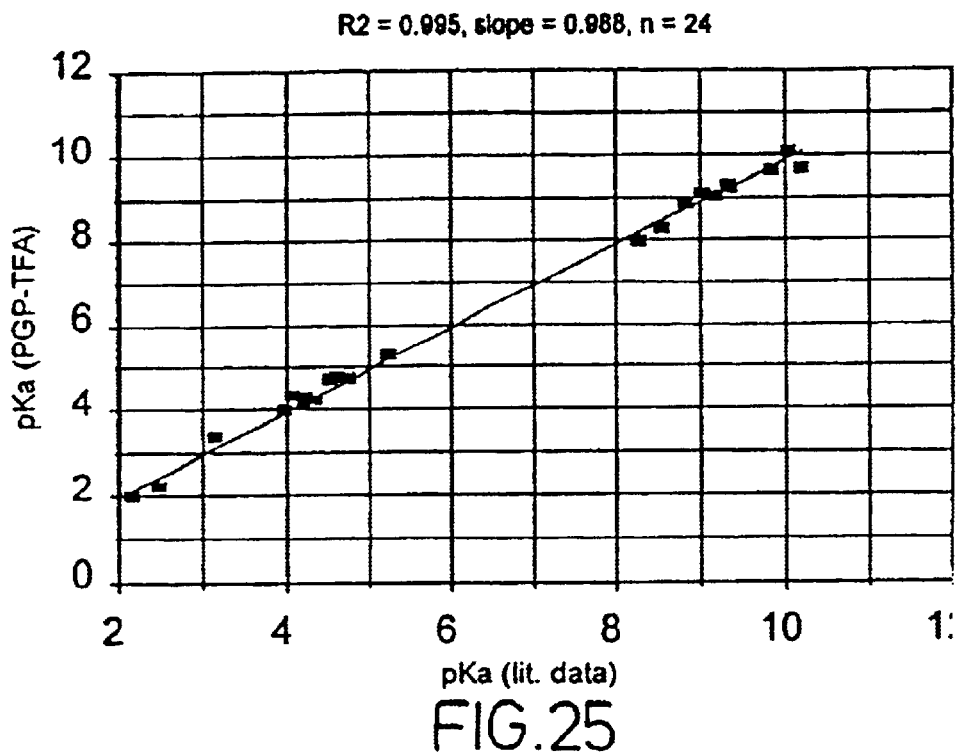
FIG. 25 is a plot of pKa as determined using the apparatus of FIG. 8 vs. Literature pKa values for 10 compounds.
Figure 26:
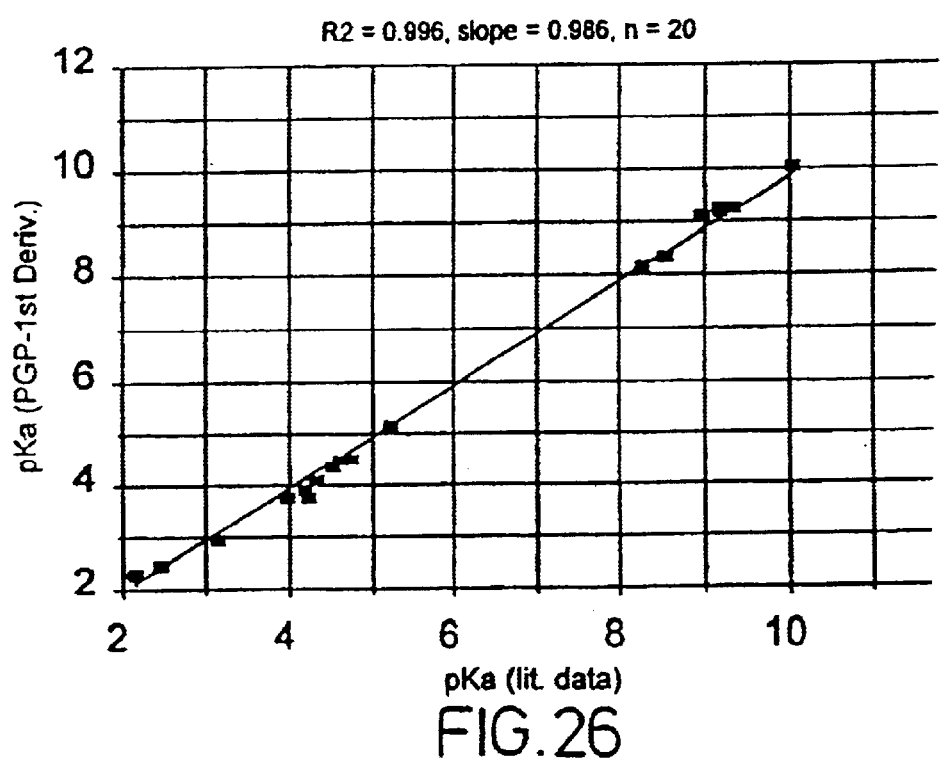
FIG. 26 is a plot of pKa as determined using the apparatus of FIG. 8 vs. Literature pKa values for a further 10 compounds.
Figure 27:
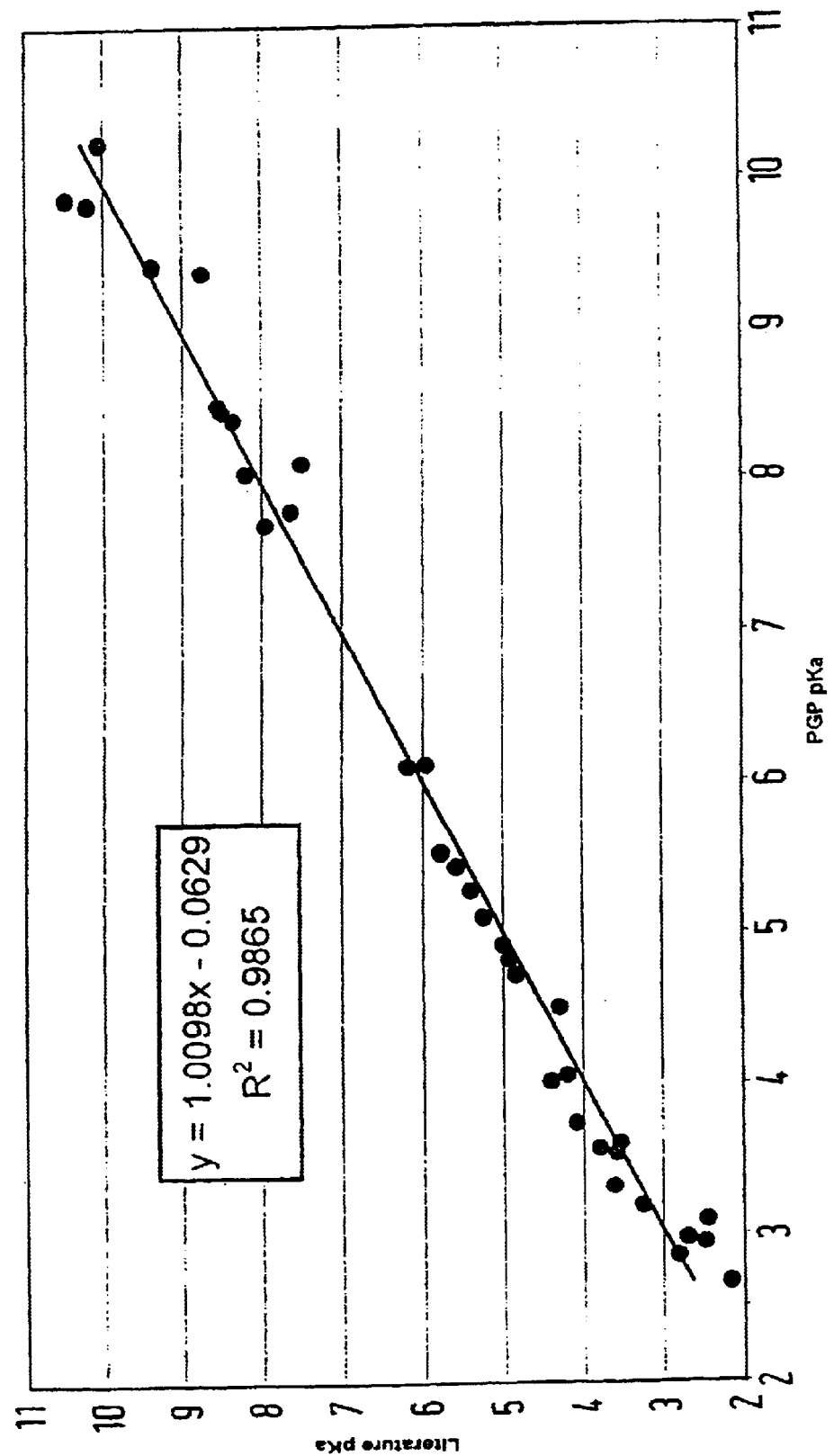
FIG. 27 is a plot of pKa as determined using the apparatus of FIG. 8 vs. Literature pKa values for 35 compounds.

As can be seen from FIGS. 25–27, the continuous titration method has proven an accurate method for determination of pKas across a wide pH range and for compounds with multiple pKas which have been difficult to determine by traditional methods.

Example 3

Determination of Partitioning Into Micelles

An important attribute of certain drug molecules is that they may partition across certain barriers, such as phospholipid membranes. Generally, one of the ionisation states of a given molecule will cross the barrier more efficiently than the other(s). At a given pH, a certain constant proportion of the molecules in free solution will be ionised, but individual molecules will be switching between ionised and unionised states: it is a dynamic equilibrium. If, for example, the unionised form has the greater tendency to partition into the micelles, then the addition of micelles causes the concentration of that species in free solution to drop, as the molecules cross into the micelles. The dynamic equilibrium between the ionised and unionised forms in the free solution adjusts to this, by a drop in the concentration of the ionised species and a rise in the concentration of the unionised species, until the initial equilibrium ratio is re-established. Thus the observed absorbance mid-point (apparent pKa) is shifted when a pH gradient is run in the presence of micelles. This results in an observed shift in the pKa of the compound, increasing for acids, decreasing for bases. The log P of the compound can be derived directly from this shift in apparent pKa and a knowledge of the volume ratios of the two phases. One assumption of this approach is that the absorption characteristics of the molecules do not change significantly between phases.

This behaviour can be studied using the continuous titration method and apparatus described above by including a fourth component in the gradient mixture. This component comprises micelles formed from surfactants such as sodium dodecyl sulphate (SDS). The concentration of surfactant in the fourth component must be high enough that in the final test stream, mixed from the four components, the surfactant is present in excess of its critical micelle concentration (CMC) and micelles are formed.

To determine partitioning, the amounts of the micelles suspension and of the sample solution are maintained constant as the pH gradient is run. The partitioning coefficient can be determined by the following equation:

$$\log P = \log (\Delta pKa \, (Vw/Vo))$$

where $\Delta pKa$ is the difference in pKa in the presence and absence of micelles, Vw is the volume of the aqueous phase and Vo is the volume of the organic phase (micelles). Vo can be calculated from the CMC, micelle radius and the aggregation number of the surfactant (number of molecules required for each micelle), factors which would be readily available to or calculable by the skilled man.

Partitioning of Benzoic Acid into SDS Micelles

This experiment was run to observe partitioning into micelles using continuous titration. The continuous titration apparatus was set up as in Example 1 (FIG. 2).

Four concentrations of SDS were used, derived from a 0.1M stock solution in water.

The following samples were prepared, in a total volume of 20 ml.

| Sample | Volume SDS Stock (cm³) | Volume Benzoic Acid Stock (cm³) | Volume H₂O (cm³) | Conc. SDS (M) | Conc. Benzoic Acid (mM) |
|---|---|---|---|---|---|
| A | 0 | 20 | 0 | 0 | 0.77 |
| B | 20 | 0 | 0 | 0.1 | 0 |
| C | 20 | 0* | 0 | 0.1 | ~0.7 |
| D | 15 | 0 | 5 | 0.075 | 0 |
| E | 15 | 5 | 0 | 0.075 | 0.19 |
| F | 10 | 0 | 10 | 0.05 | 0 |
| G | 10 | 10 | 0 | 0.05 | 0.39 |
| H | 5 | 0 | 15 | 0.025 | 0 |
| I | 5 | 15 | 0 | 0.025 | 0.58 |

*~0.5 mg solid benzoic acid

The continuous titration apparatus was set up with the following sample queue:

| | |
|---|---|
| 1. | Blank (water only) |
| 2. | Blank (water only) |
| 3. | Blank (water only) |
| 4. | STD1 |
| 5. | STD2 |
| 6. | A |
| 7. | B |
| 8. | C |
| 9. | D |
| 10. | E |
| 11. | F |
| 12. | G |
| 13. | H |
| 14. | I |
| 15. | STD1 |
| 16. | STD2 |
| 17. | Blank (water only) |
| 18. | Blank (water only) |

The vials containing no benzoic acid (SDS blanks) did not show any titration curves and so have been omitted from any further handling (vials 7, 9, 11 and 13).

The results are summarised below:

Standard Curve

| Vial | | Compound | pKa | Time to Peak |
|---|---|---|---|---|
| 4 | STD1 | KHP | 4.878 | 299.5 |
| | | Phenol | 9.721 | 447.8 |
| 5 | STD2 | Benzoic acid | 3.964 | 272 |
| | | p—NO₂ phenol | 6.869 | 363.8 |
| 15 | STD1 | KHP | 4.878 | 300.5 |
| | | Phenol | 9.721 | 448.5 |
| 16 | STD2 | Benzoic acid | 3.964 | 272.5 |
| | | p-NO₂ phenol | 6.869 | 363.5 |

Intercept = −4.9325
Slope = 0.0326

Samples

| Vial | Compound (conc. SDS) | Time to Peak | pKa1 | Delta pKa |
|---|---|---|---|---|
| 6 | Benzoic acid (0.0M) | 271 | 3.91 | |
| 8 | Benzoic acid (0.02M) | 275.8 | 4.07 | 0.16 |
| 10 | Benzoic acid (0.015M) | 275.8 | 4.07 | 0.16 |
| 12 | Benzoic acid (0.01M) | 274.5 | 4.02 | 0.11 |
| 14 | Benzoic acid (0.005M) | 274 | 4.01 | 0.10 |

Calculation of Log P $$\log P = \log (\Delta pKa \times Vw/Vo)$$

where
  Vw = volume of aqueous phase
  Vo = volume of organic phase

For this exercise Vo is taken as the volume of SDS micelles.

At 0.1M ionic strength (the ionic strength of the buffer stream)
  Micelle radius = $2.5 \times 10^{-9}$ m
  Aggregate number — ~100
  Critical Micelle Concentration: 1.5 mM.

(From Van Os N. M. et.al: Physico-chemical properties of selected Anionic, Cationic and non-ionic surfactants. Elsevier ISBN:0-444-89691-0).

All surfactant present above the CMC is present in the form of micelles, so from the above information we can calculate the volume of SDS micelles present in each solution.

Volume of Sphere $$V = \frac{4\pi r^3}{3} = 6.54 \times 10^{-26} \text{ m}^3$$

| Sample | pKa | Final SDS conc. (Molar) | SDS excess (Molar) | SDS molecules | SDS micelles | SDS volume (ml) | Vol. Ratio | Delta pKa | P | log P |
|---|---|---|---|---|---|---|---|---|---|---|
| Benzoic acid | 3.91 | | | | | | | | | |
| Benzoic acid in 0.1M SDS | 4.07 | 0.02 | 0.0185 | $1.11 \times 10^{22}$ | $1.11 \times 10^{20}$ | 0.00729 | 137.25 | 0.16 | 21.96 | 1.34 |
| Benzoic acid in 0.075M SDS | 4.07 | 0.015 | 0.0135 | $8.13 \times 10^{21}$ | $8.13 \times 10^{19}$ | 0.00532 | 188.08 | 0.16 | 30.09 | 1.48 |
| Benzoic acid in 0.05M SDS | 4.02 | 0.01 | 0.0085 | $5.12 \times 10^{21}$ | $5.12 \times 10^{19}$ | 0.00335 | 298.72 | 0.11 | 32.86 | 1.52 |
| Benzoic acid in 0.025M SDS | 4.01 | 0.005 | 0.0035 | $2.11 \times 10^{21}$ | $2.11 \times 10^{19}$ | 0.00138 | 725.46 | 0.1 | 72.55 | 1.86 |

Average log P = 1.55
Stdev 0.11

The experiment appears to have worked very well, a consistent shift in pKa was observed, which gives reasonable results in all SDS concentrations.

These results indicate that continuous titrations can be used for measuring partitioning into organised organic phases such as micelles.

Example 4
End Point Titration—Apparatus of FIG. 2

Many traditional quantitative titration techniques, for example determination of the concentration of a compound in a solution, rely upon the use of a visual endpoint indicator. The accuracy of such techniques are heavily reliant upon the skill of the operator and visual interpretation of the endpoint indicator. Using continuous gradient titration with spectroscopic detection of endpoints will make the accuracy of the technique independent of operator skills. The technique will be especially applicable to compounds with a single ionisable group or a small number of non-overlapping pKas.

An example of the use of this technique is the determination of potassium hydrogen phthalate (KHP) concentration by endpoint determination using phenolphthalein indicator. KHP is strongly acidic in solution. It can be quantified by titration against a strong base; when all the KHP has been titrated out, there is a sharp rise in pH which is detected by the presence of phenolphthalein indicator which undergoes a colour change from colourless to pink and over the pH range 8.4 to 10.0.

The test solute (KHP) was introduced in the sample stream of the apparatus of FIG. 2 at a constant 20% of the final mixture, as in Example 2 above. The two components of the gradient (from 80% to zero and zero to 80% respectively) are 0.05M KOH and water. The end-point indicator was introduced via the sample stream (2 drops phenolphthalein solution in 20 cm³ of sample).

The test solute KHP was titrated by the KOH stream. As soon as all compound has been titrated there is a large increase in pH and rapid change of the ionisation state of the indicator and hence a rapid colour change. The system was calibrated by the use of KHP standards of known concentration.

Chemicals
  0.05M KOH—channel B
  50 cm³ 0.5-KOH (Aldrich) diluted to 500 cm³ in H₂O
  0.27 g phenolphthalein indicator weighed out and dissolved in 10 cm³ MeOH and 10 cm³ H₂O. Some precipitation did occur.
  KHP solution 0.1416M
  A series of dilutions were made to yield the following KHP solutions
  0.1416M
  0.0708M
  0.0354M
  0.0177M
  0.0089M These standards were decanted into scintillation vials and 2 drops of indicator added. The samples and a blank were then run. Absorbance was measured at 240 nm.

Figure 16:
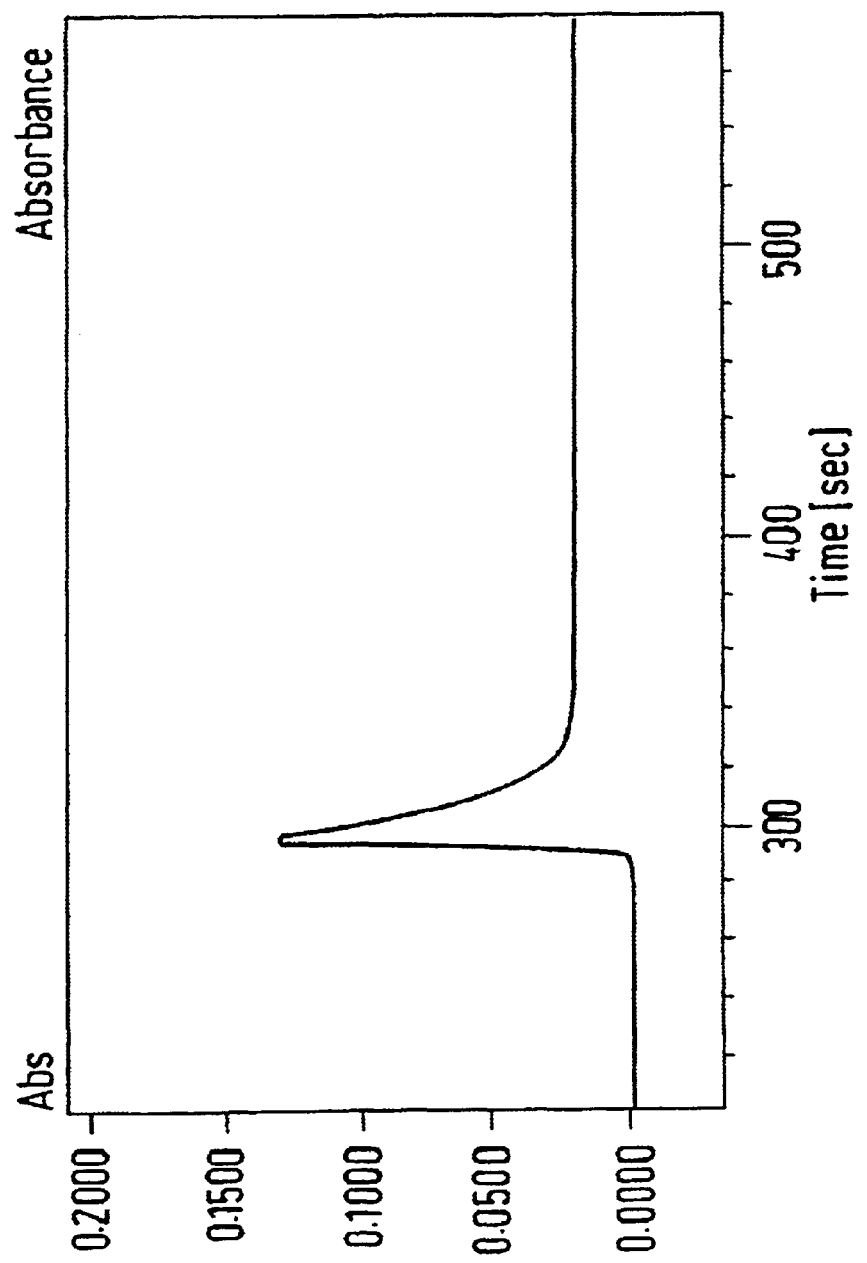
FIG. 16 is an absorbance curve for an endpoint titration (Example 4)

Example traces obtained are shown in FIG. 16.

The peak times obtained for the blank and standards were entered into an Excel spreadsheet and a regression of KHP concentration against gradient time performed.

| Determination of KHP by Continuous Gradient Titration ||
|---|---|
| Conc. KHP (M) | Peak Time |
| 0.1416 | 398 |
| 0.0708 | 292 |
| 0.0354 | 241 |
| 0.0177 | 216.5 |
| 0.0089 | 203.5 |
| 0 | 186.5 |

Figure 17:
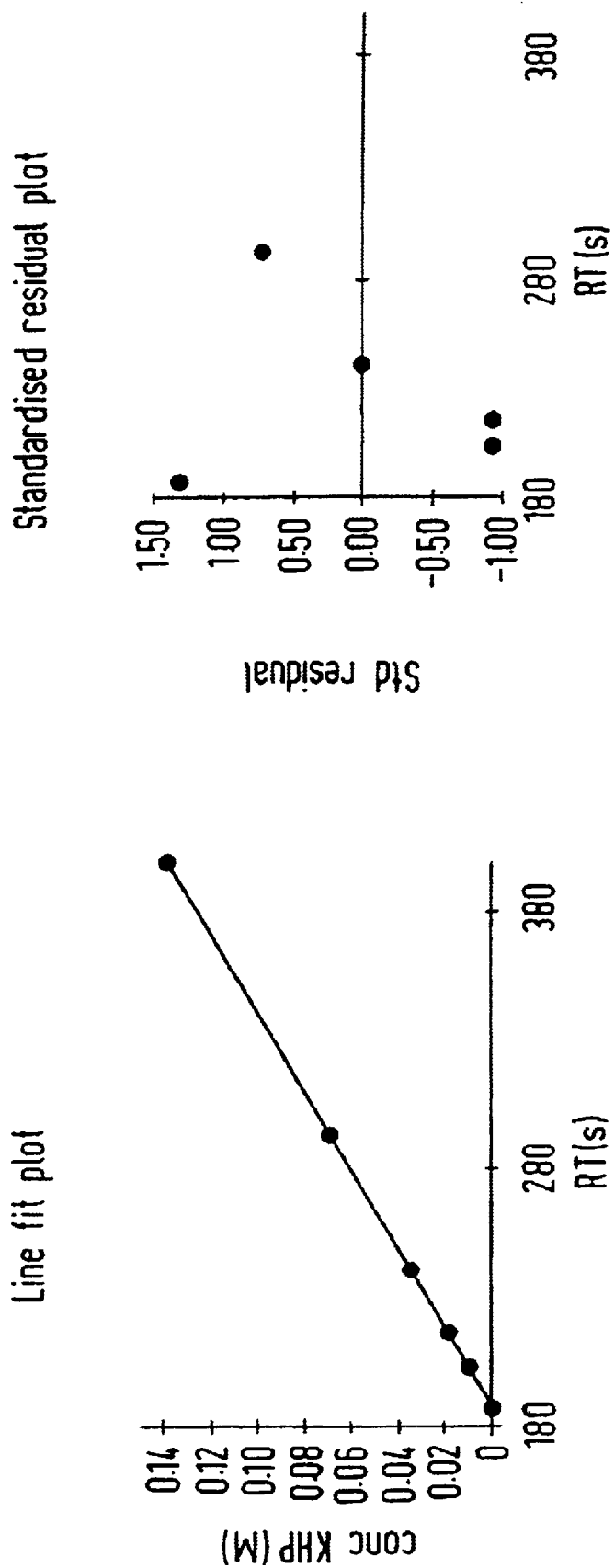
FIG. 17 is a calibration curve for an endpoint titration (Example 4)

A very good regression was obtained with highly significant statistics $r^2=0.9996$ F=10337—the calibration curve plotted is shown in FIG. 17. Unknown concentrations of KHP run on the same gradient can be determined from this 1st derivative peak absorbance time using this calibration curve.

This experiment has shown the applicability of continuous gradient titration to classical end-point titrations.

This approach should have several benefits over traditional approaches.

1. Fast, high throughput;
2. Very sharp end-point detection, high accuracy;
3. No user knowledge required;
4. Large dynamic range.

Example 5
KHP Endpoint Determination—Apparatus of FIG. 8

Solutions

Phenolphthalein indicator:

0.33 g phenolphthalein dissolved in 10 $cm^3$ MeOH and 10 $cm^3$ $H_2O$. Excess phenolphthalein precipitates out with time.

KOH titrant:

50 ml of 0.5 N KOH (Aldrich) diluted into 500 $cm^3$ distilled $H_2O$ to give a stock solution of concentration 0.05N KOH.

KHP stock solution:

7.723 g KHP (molecular weight 204.23) dissolved in 250 $cm^3$ $H_2O$ to give a solution of concentration 0.15126M.

A series of standards was prepared from the KHP stock solution.

| Standard | Vol. Stock | Vol. $H_2O$ | Final Concentration |
|---|---|---|---|
| A | 2 $cm^3$ | 8 $cm^3$ | 0.030252 M |
| B | 4 $cm^3$ | 6 $cm^3$ | 0.060504 M |
| C | 6 $cm^3$ | 4 $cm^3$ | 0.090756 M |
| D | 8 $cm^3$ | 2 $cm^3$ | 0.121008 M |
| E | 10 $cm^3$ | 0 $cm^3$ | 0.151260 M |

KHP Samples:

A set of KHP samples was prepared from the stock solution, the composition of which was not revealed until after the experiment:

| Standard | Vol. Stock | Vol. $H_2O$ | Final Concentration |
|---|---|---|---|
| 1 | 2.3 $cm^3$ | 10 $cm^3$ | 0.028 M |
| 2 | 3.98 $cm^3$ | 10 $cm^3$ | 0.043 M |
| 3 | 1.86 $cm^3$ | 10 $cm^3$ | 0.024 M |
| 4 | 3.3 $cm^3$ | 10 $cm^3$ | 0.038 M |
| 5 | 4.32 $cm^3$ | 10 $cm^3$ | 0.46 M |
| 6 | 1.65 $cm^3$ | 10 $cm^3$ | 0.021 M |

Experimental Set up:

DAD 440 Detector:

The diode away detector was set up to detect at four wavelengths: 540 nm, 550 nm, 560 nm and 570 nm.

Syringe Module:

| Solvent A: | $H_2O$ |
|---|---|
| Solvent B: | 0.05 N KOH |

The solvents were dispensed from 5 $cm^3$ syringes. The flow rate through the flow cell was 0.8 $cm^3$ $min^{-1}$. Gradient time was 240s with a pre-gradient flow of 75s and post-gradient flow of 90s followed by a post-gradient restoration period of 45s, giving a 7.5 minute cycle time overall.

The autosampler was set up with a dispensing rate of 0.2 $cm^3$ $min^{-1}$ and a 7.5 minute cycle time. Blanks, standards and samples were run in the following order:

| | |
|---|---|
| 1 | Blank |
| 2 | Blank |
| 3 | Blank |
| 4 | Standard A |
| 5 | Standard B |
| 6 | Standard C |
| 7 | Standard D |
| 8 | Standard E |
| 9 | Sample 1 |
| 10 | Sample 2 |
| 11 | Sample 3 |
| 12 | Sample 4 |
| 13 | Sample 5 |
| 14 | Sample 6 |
| 15 | Sample 1 |
| 16 | Sample 2 |
| 17 | Sample 3 |
| 18 | Sample 4 |
| 19 | Sample 5 |
| 20 | Sample 6 |
| 21 | Blank |
| 22 | Standard A |
| 23 | Standard B |
| 24 | Standard C |
| 25 | Standard D |
| 26 | Standard E |
| 27 | Blank |

The data was captured using Dasylab and analysed using the first derivative method following 3 data point smoothing. The data was analysed at 540 nm.

| Vial | Sample | (M KHP) | Time to 1st Derivative Maximum (s) | Conc. KHP (M) From Std Curve |
|---|---|---|---|---|
| 1 | Blank | 0.000 | | |
| 2 | Blank | 0.000 | | |
| 3 | Blank | 0.000 | 129.8 | |
| 4 | A | 0.030 | 159.0 | |
| 5 | B | 0.061 | 189.8 | |
| 6 | C | 0.091 | 224.5 | |
| 7 | D | 0.121 | 258.5 | |
| 8 | E | 0.151 | 295.8 | |
| 9 | S1 | | 155.3 | 0.023 |
| 10 | S2 | | 167.0 | 0.034 |
| 11 | S3 | | 152.3 | 0.020 |
| 12 | S4 | | 162.3 | 0.029 |
| 13 | S5 | | 169.5 | 0.036 |
| 114 | S6 | | 151.8 | 0.020 |
| 15 | S1 | | 155.0 | 0.023 |
| 16 | S2 | | 165.5 | 0.032 |
| 17 | S3 | | 152.3 | 0.020 |
| 18 | S4 | | 162.0 | 0.029 |
| 19 | S5 | | 170.0 | 0.036 |
| 20 | S6 | | 151.0 | 0.019 |
| 21 | Blank | 0.000 | 129.3 | 0.000 |
| 22 | A | 0.030 | 158.8 | |
| 23 | B | 0.061 | 189.5 | |
| 24 | C | 0.091 | 224.5 | |
| 25 | D | 0.121 | 259.5 | |
| 26 | E | 0.151 | 295.0 | |
| 27 | Blank | 0.000 | 131.7 | |

Figure 19:
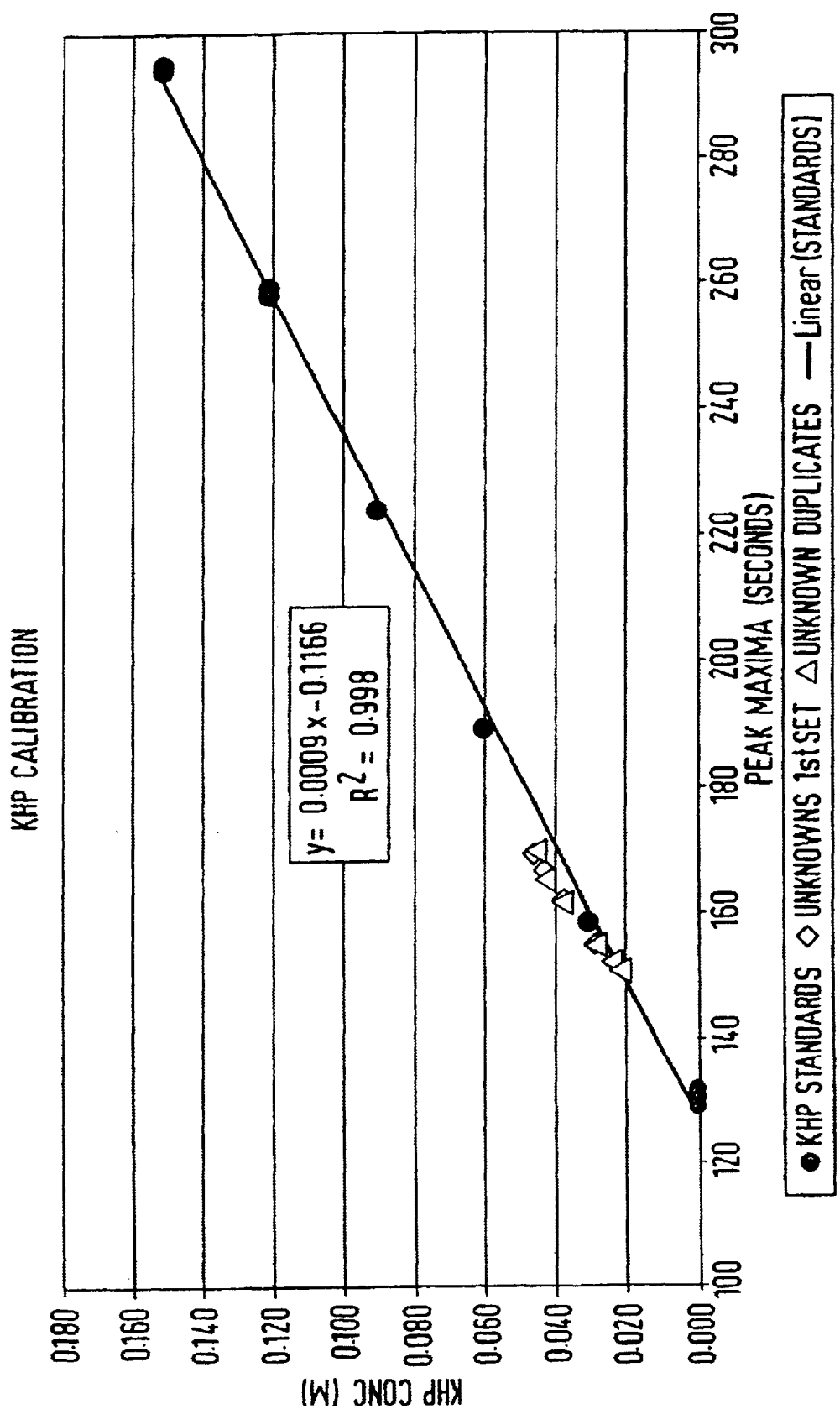
FIG. 19 is a calibration curve for an endpoint titration (Example 5)

The standard curve was plotted (see FIG. 19) and can be represented by the equation $$y=0.009x-0.1166\ R^2=0.998$$

Using the calibration curve plotted from the standard solutions, the times of the first derivative maxima for each sample can be converted into sample concentrations for the above table. Comparing the results (averaged for the duplicate samples) with the calculated compositions of the samples:

| Sample No. | Calculated Sample Concentration | Determined Sample Concentration |
|---|---|---|
| 1 | 0.028 | 0.023 |
| 2 | 0.043 | 0.033 |
| 3 | 0.024 | 0.020 |
| 4 | 0.038 | 0.029 |
| 5 | 0.046 | 0.036 |
| 6 | 0.021 | 0.020 |

Example 6

EDTA Complexometric Titration of $Zn^{++}$ using Xylenol Orange as an Indicator

This method is loosely based upon a methodology developed by S G Novick for the determination of zinc in throat lozenges J. Chem. Ed—Vol. 74 (12) 1463 (1997).

Zinc ions form a complex with Xylenol orange to give an intense red colour absorbing at 580 nm. When titrating with EDTA (ethylenediaminetetracetic acid), the $Zn^{++}$ preferentially forms a complex with the EDTA. Once all the $Zn^{++}$ has formed the EDTA-$Zn^{++}$ complex, then the Xylenol orange is once again in the free form, which is yellow in appearance and so a corresponding decrease in absorbance at 580 nm is observed.

Solutions:

Xylenol orange indicator:

0.1% in $H_2O$=100 mg in 100 $cm^3$.

EDTA solution:

For a 500 $cm^3$ 18.75 mM stock solution, 3.485 g EDTA.2Na.2$H_2O$ (molecular weight 372.24) is dissolved in 500 $cm^3$ $H_2O$.

Zinc standards:

Zinc nitrate was chosen as the salt for formation of the standards. The concentration of the zinc in the test mixture stream must be less than the maximum concentration of the EDTA, to ensure that all zinc is complexed by the EDTA, leaving the indicator in the free, uncomplexed form. At its maximum, the EDTA solution will make up 80% of the stream, at a concentration of 18.72×0.8=14.976 mM.

Thus the $Zn^{++}$ concentration in the measurement stream must be less than 14.976 mM. The zinc samples will make up 20% of the stream, so the maximum concentration of zinc ions in the samples must be 14.976×100÷5=74.88 mM.

1.03 g of $Zn(NO_3)_2.6H_2O$ was weighed out and dissolved in 50 $cm^3$ 0.1N acetate buffer (pH 4.9) to give a zinc stock solution of concentration 69.25 mM. From this, standards were prepared:

| Standard* | Volume of Stock Solution | Volume $H_2O$ | Concentration (mM) |
|---|---|---|---|
| A | 2 $cm^3$ | 8 $cm^3$ | 13.85 |
| B | 4 $cm^3$ | 6 $cm^3$ | 27.70 |
| C | 6 $cm^3$ | 4 $cm^3$ | 41.55 |
| D | 8 $cm^3$ | 2 $cm^3$ | 55.40 |
| E | 10 $cm^3$ | 0 $cm^3$ | 69.25 |

*200 µl xylanol orange indicator was added to each standard

Gradient:

| Syringe A: | $H_2O$ |
|---|---|
| Syringe B: | 18.72 mM EDTA stock solution |
| Flow rate: | 0.8 $cm^3$ $min^{-1}$ |

Gradient time:

240s 100% A to 100% B with a pre-gradient dispensing time of 75s (Syringe A), a post-gradient dispensing time of 90s (Syringe B) and a post-gradient restoration time of 45s (Syringe A). This gives a 7.5 minute cycle time.

Figure 20:
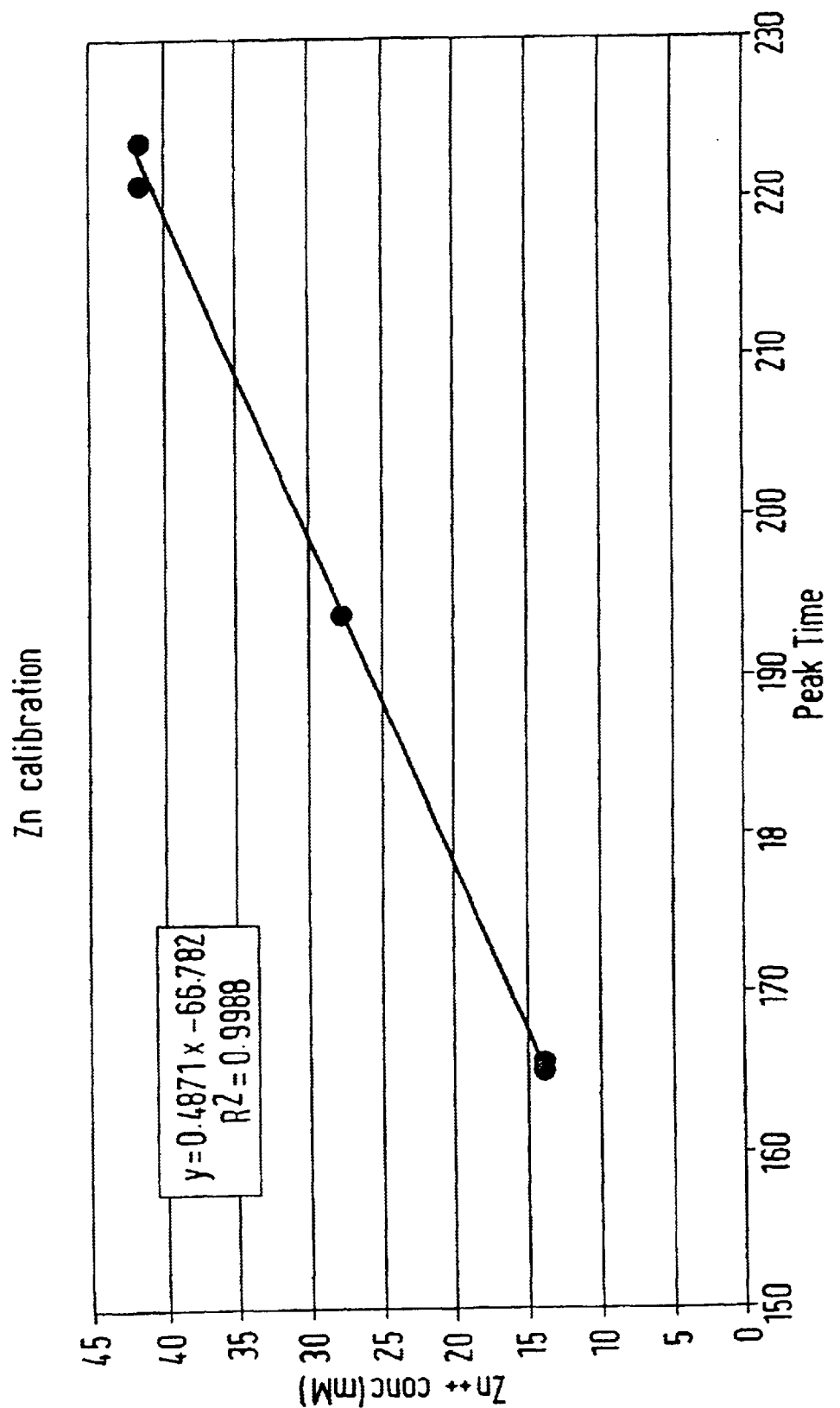
FIG. 20 is a calibration curve for a complexometric titration (Example 6)
Figure 21:
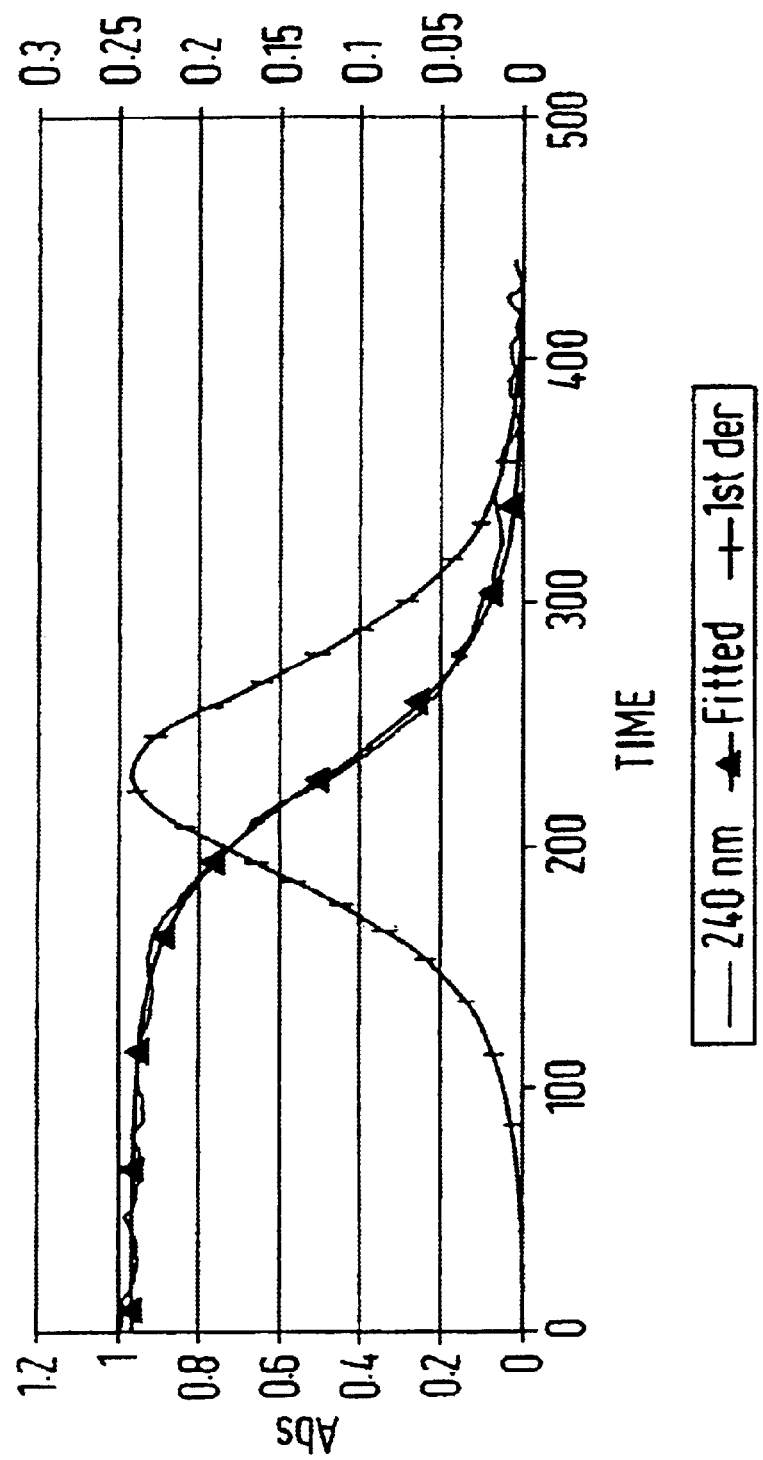
FIGS. 21 to 24 show the use of curve fitting as a data processing method.
Figure 22:
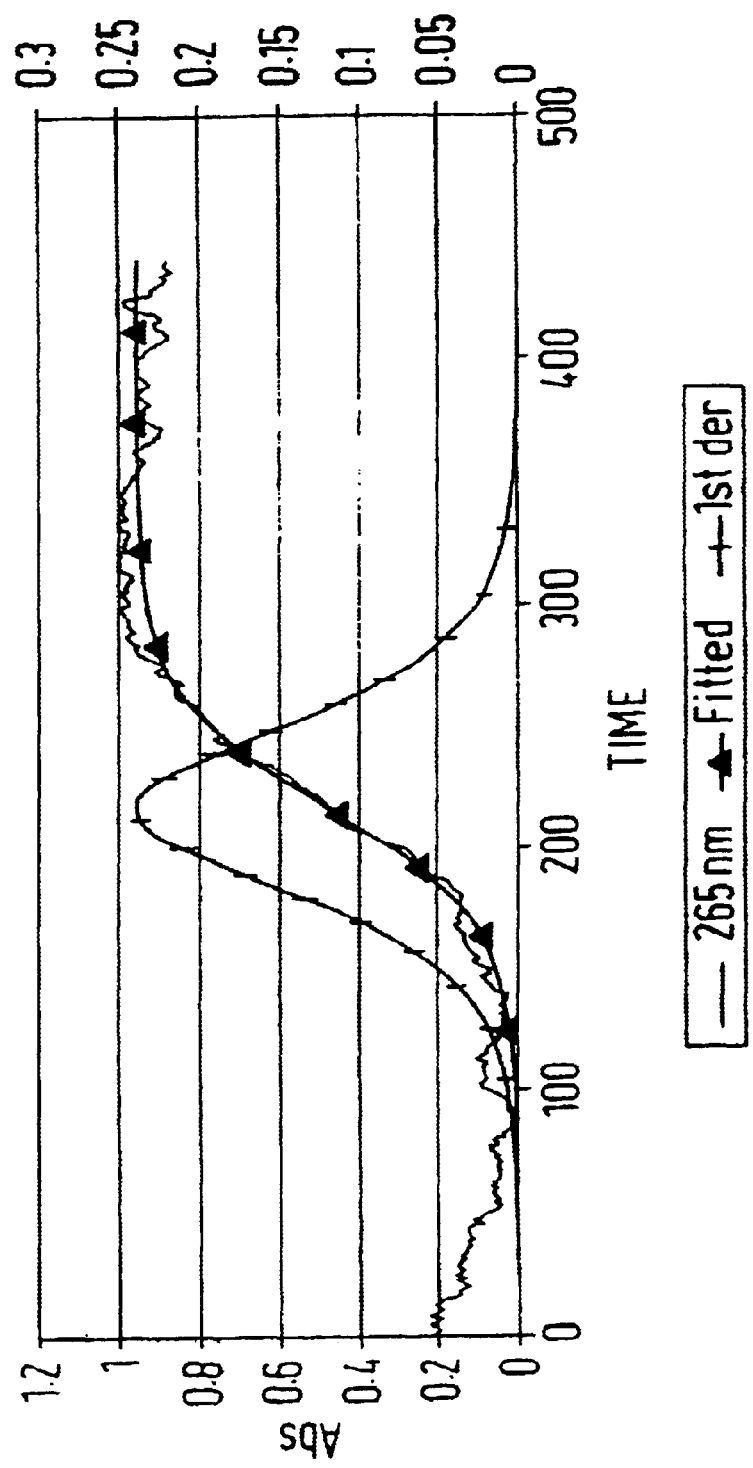
Figure 23:
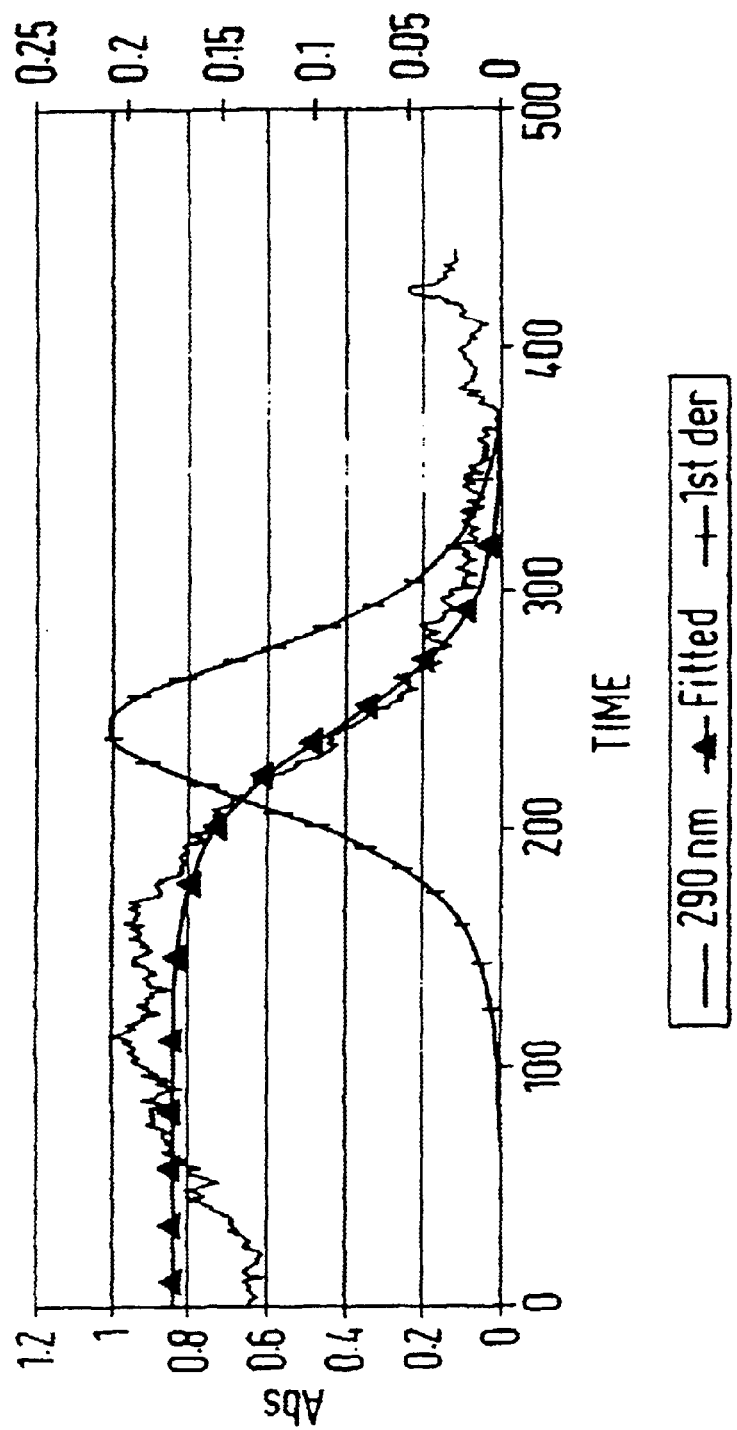
Figure 24:
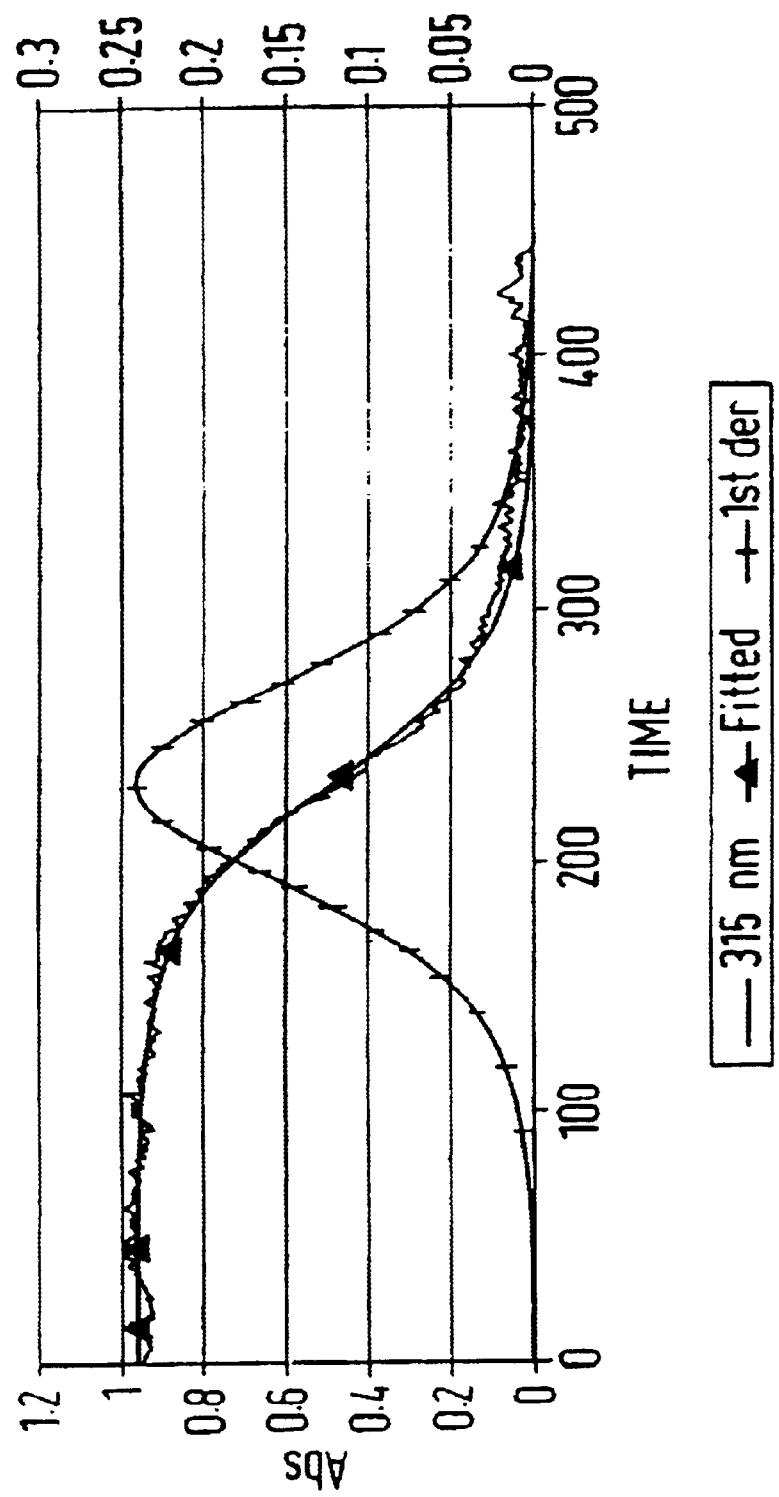

The autosampler was set up with the 7.5 minute cycle time and a 0.2 mM $min^{-1}$ dispensing rate and the standards were run against the EDTA gradient to establish a calibration curve (see FIG. 20). The peak times in the first derivative of the absorbance data at 570 nm were as follows:

| Vial | Solution | Peak Time |
|---|---|---|
| 1 | Blank | — |
| 2 | Blank | — |
| 3 | Standard A | 165.3 |
| 4 | Standard A | 165.8 |
| 5 | Standard B | 194.0 |
| 6 | Standard B | 194.0 |
| 7 | Standard C | 221.0 |
| 8 | Standard C | 223.7 |
| 9 | Standard D | NF |
| 10 | Standard D | NF |
| 11 | Standard E | NF |
| 12 | Standard E | NF |

NF = 1st derivative curve not fitted

The first derivative curve could not be fitted to the absorbance data involving high concentration standards. This is thought to be due to insufficient buffering of the standard solutions, which therefore did not give a clear colour change in the xylenol orange indicator. For the first 3 standards, where results could be obtained, a linear calibration curve was obtained (FIG. 20). This experiment shows clearly that the continuous titration method can be used for complexometric titrations. In the example shown here buffering capacity was insufficient, but this could be improved by using buffer for making up the EDTA solution.

Example 7

Application of Curve Fitting to pKa Data Generated by the Continuous Titration Method Analysis of the absorbance data generated by the continuous titration method and apparatus can be by the first derivative method discussed above. For this method to be used successfully, the absorbance data needs to be smoothed which results in data at the extremes of the titration being lost. However, the first derivative method works very well when the absorbance changes are large, the pH gradient is very linear and there are no overlapping pKas. A second technique which may be applied to the data analysis is target factor analysis (TFA). This method is better suited to multiple, especially overlapping pKas, but is computationally intensive and requires spectral data at several wavelengths. Also, the ionisation behaviour of the sample molecule needs to be understood before the data can be processed.

The third method of analysis which can be applied to the data generated in the continuous titration spectroscopic methods of the present invention is "curve fitting". This method of analysis can be used with much smaller spectral changes, is fairly insensitive to non-linearity in the pH gradient, requires data from only a single wavelength, does not require data smoothing and is not very computationally intensive. In the following example, absorbance data from the titration of a sample compound S, obtained using a linear pH gradient formed as in Example 2, was normalised as described below. Data from four wavelengths was used. The minimum and maximum absorbance for each wavelength was determined and the data scaled between zero and one, using the equation:

$$Abs_{new} = \frac{Abs_{obs} - Abs_{min}}{(Abs_{max} - Abs_{min})}$$

The spectral change can be defined as a logistic function:

$$Abs = \frac{A}{(1 + B^{(-D \ast x^-)})}$$

In which A, B and D are constants and x is the dependant variable. In the example below A, B, and D are found by trial and error fitting, and x is time. This function was fitted to the spectral data using the "solver" function in Microsoft Excel™, by minimising the residual sums of squares and fitting A, B and D.

The data for the four wavelengths is summarised below:

| λ | A | B | D | RSS |
|---|---|---|---|---|
| 240 | 0.9713 | 0.0003 | −0.0349 | 0.1660 |
| 265 | 0.9539 | 10609 | 0.0429 | 1.757 |
| 290 | 0.8372 | 1.63E$^{-5}$ | −0.0455 | 3.4240 |
| 315 | 0.9577 | 0.00025 | −0.0359 | 0.2528 |

If B is large then absorbance increases with time. If B is small then absorbance decreases with time.

The first derivative of the logistic is defined as:

$$Abs = \frac{A}{(1 + B^{(-D \cdot x^-)})^2} \cdot b^{(-D \cdot x)}$$

By finding the datapoint correlating to the 1st derivative maximum we can use the data as normal 1st derivative data, calibrating against standards of known pKa.

Summary of Sample S data:

| | 240 nm | 265 nm | 290 nm | 315 nm |
|---|---|---|---|---|
| Abs$_{min}$ | −0.2315 | −0.001 | −0.00245 | −0.00663 |
| Abs$_{max}$ | −0.00028 | 0.003967 | 0.0013 | 0.0043 |
| Range | 0.02286 | 0.00497 | 0.00378 | 0.00706 |

As can be seen, all of the spectral changes are very small.

| | 240 nm | 265 nm | 290 nm | 315 nm |
|---|---|---|---|---|
| A | 0.9713 | 0.9539 | 0.8372 | 0.95577 |
| B | 0.0003 | 10609 | 1.63E$^{-5}$ | 0.00025 |
| D | −0.0349 | 0.0429 | −0.0455 | −0.0359 |
| RSS | 0.1660 | 1.757 | 3.4240 | 0.2528 |

-continued

| | 240 nm | 265 nm | 290 nm | 315 nm |
|---|---|---|---|---|
| Data pt. for max. 1st derivative: | 230 | 216 | 242 | 231 |

By using the range used in the normalisation procedure, the values can be weighted:

| λ | Range | 1st Derivative Max. |
|---|---|---|
| 240 | 0.023 | 230 |
| 265 | 0.005 | 216 |
| 290 | 0.004 | 242 |
| 315 | 0.007 | 231 |
| | | Average: 229.75 |
| | | *Weighted Av: 229.56 |

*Weighted Av. Produced using "sum product" function in Microsoft Excel ™

The raw data, fitted curves and (for comparison) first derivative curves are plotted for each wavelength in FIGS. 21 to 24.

Example 8
Theoretical Investigation into the Determination of Partition Coefficients When pKas are determined in the presence of an immiscible solvent, there is a shift in the "apparent" pKa value obtained. This shift is caused by the partitioning of the compound into the organic phase. The size of the shift is dependent upon the partition coefficient of the compound and the ratio of the volumes of the two phases.

The partition coefficient (log P) can be found from the following equation:

$$\log P = \log (10^{ch}(pKa-pKa')-1)/R$$

where:
pKa=pKa in H$_2$O
pKa'=pKa in the presence of organic phase
ch=charge in molecule (−1 for acids, +1 for bases)
R=volume ratio=volume of organic phase÷volume of aqueous phase.

This model only holds true for monoprotic compounds.

If the volume ratios are equivalent then log P is approximately equivalent to the difference between pKa and pKa'.

The continuous titration apparatus may be used for determining log P values by carrying out two titrations, the first a standard continuous titration as in Example 1 and the second with the addition of an octanol or other organic phase stream in contact with the aqueous sample stream. Given an adequate contact area between the aqueous and organic streams, partitioning will occur between the two phases. The aqueous and organic phases are then separated and the aqueous stream passed through the detector.

One means of achieving this is to use the microscale chemical processing device being developed by CRL and BNFL. This device is specifically designed to allow aqueous and organic phases to flow in contact with each other and then be clearly separated. Details may be found in "Eureka, Transfers Technology" Oct. 1997, page 42. If equal flow rates are used, this will be equivalent to equal volume ratios in a traditional partitioning experiment. The spectral data which would be expected from such an experiment can be modelled as follows:

For any given pH, the log D of a monoprotic compound can be modelled as follows:

$$\log D = \log(10^{\log P} + 10^{\log P - \Delta + ch(pKa - pH)}) - \log(1 + 10^{ch(pKa - pH)})  \quad \text{Eq.1}$$

where:
log P=log P of unionised species
Δ=log P of unionised species minus log P of ionised species
ch=charge (−1 for acids, +1 for bases)
pKa=pKa of molecule.

The absorbance of the solution at any given pH can be modelled by:

$$A = \frac{\% \text{ ionised}}{\square} \times A_1 + \frac{100 - \% \text{ ionised}}{100} \times A_0 \quad \text{Eq. 2}$$

where:
$A_I$=absorbance of the ionised species and
$A_0$=absorbance of the unionised species.

In the partitioning experiment the concentration of compound in the aqueous phase can be modelled by:

$$\text{conc}_{aq} = 1/10^{\log D} + 1 \quad \text{Eq.3}$$

and the concentration of the octanol phase by $$\text{conc}_{oct} = 1 - \text{conc}_{aq} \quad \text{Eq.4}$$

Figure 29:
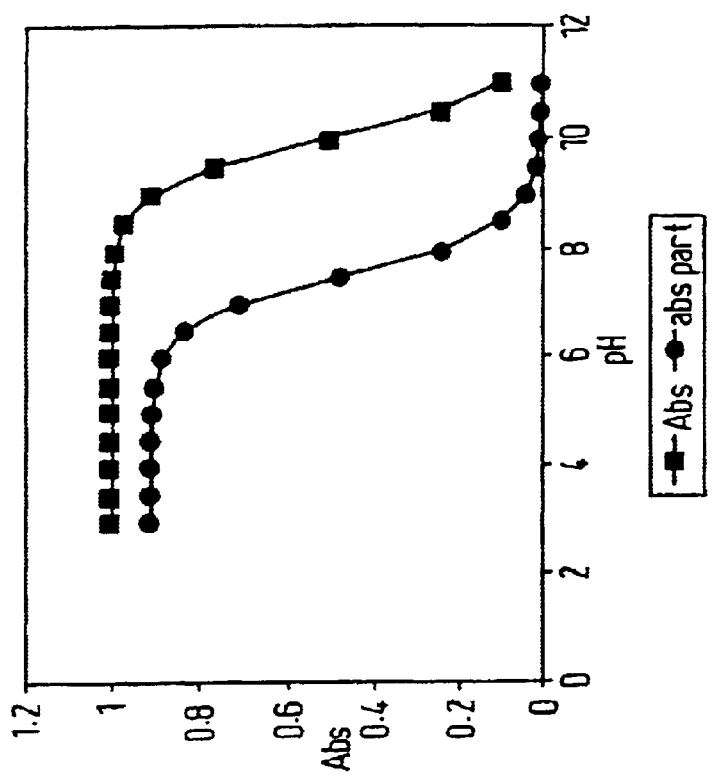
FIG. 29 shows the expected absorbance profiles with the absence and presence of partitioning base medium.
Figure 28:
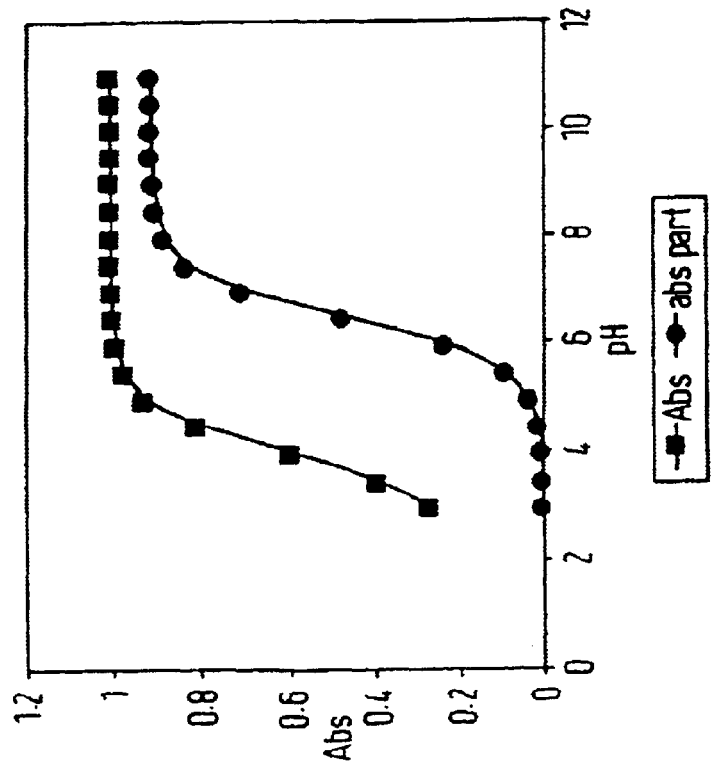
FIG. 28 shows the expected absorbance profiles with the absence and presence of partitioning acid medium.

By combining equations 2 and 3 we can model the absorbance of the aqueous phase during the partitioning experiment. Expected results for typical acids and bases would be similar to those shown in FIGS. 28 and 29.

Variation:

It will be apparent to the skilled man that variations of the above are possible, for example instead of calibrating the system using several standards run before or between the samples, the standard compounds of known pKa could be included in the sample solution to provide internal standards. These would give absorbance change times for known pKas against which the test compound could be compared. Other adaptations would be apparent to the skilled man which may be put into practice with the aid of standard laboratory techniques and without undue burden.

What is claimed is:

1. A method of continuous titration in which at least one parameter of at least one compound in a test mixture may be monitored as the composition of the mixture is continuously varied by changing the concentration of one or more species in the mixture, the method comprising the steps of continuously mixing at least two component fluid streams to form a test mixture stream and passing the test mixture stream through a spectrophotometric detection zone, characterised in that the volume to volume ratio of at least two of the component streams forming the test mixture stream is continuously and linearly varied with time by alteration of the relative proportions of the component streams forming the test mixture, whilst the total volume of the test mixture stream remains constant.

2. A method according to claim 1 wherein the test mixture stream is formed from three component fluid streams, the proportion of one component fluid stream remaining constant, the proportions of the second and third component fluid streams being variable in inverse proportion to one another.

3. A method according to claim 2 wherein the variable component streams comprise buffer solutions, test reagents, aqueous or organic solvents.

4. A method according to claim 2 wherein the spectrophotometric detection zone comprises a multiwavelength spectrophotometric detector.

5. A method according to claim 4 wherein the spectrophotometric detector is an ultraviolet or visible range spectrophotometer, a fluorimeter, a polarimeter, a colourimeter, or a light scattering, optical rotation or circular dichrosim detector.

6. A method according to claim 5, wherein the spectrophotometric detector is a scanning ultraviolet or visible range spectrophotometer.

7. A method according to claim 1 wherein the variable component streams comprise buffer solutions, test reagents, aqueous or organic solvents.

8. A method according to claim 7 wherein there are at least two variable components, comprising two linearising buffer solutions.

9. A method according to claim 8 wherein the linearising buffers are formed from acidic and basic components derived from the same compound such that the overall chemical composition of the test mixture stream remains constant during titration as the relative proportions of the two linearising buffers are changed.

10. A method according to claim 9 wherein the acidic and basic components include citric acid, potassium citrate, $KH_2PO_4$, $K_2HPO_4$, HCl and KOH.

11. A method according to claim 1 wherein the spectrophotometric detection zone comprises a multiwavelength spectrophotometric detector.

12. A method according to claim 11 wherein the spectrophotometric detector is an ultraviolet or visible range spectrophotometer, a fluorimeter, a polarimeter, a colourimeter, or a light scattering, optical rotation or circular dichrosim detector.

13. A method according to claim 12, wherein the spectrophotometric detector is a scanning ultraviolet or visible range spectrophotometer.

14. A method of continuous titration comprising mixing a flowing fluid stream comprising a compound under test mixture stream and passing the test mixture stream to form a test mixture stream and passing the test mixture stream through a spectrophotometric detection zone at which readings relating to at least one physical or chemical parameter of the compound under test are taken, characterised in that the test mixture stream is passed through the spectrophotometric detection zone at a constant flow rate and that the flow rate of at least two of the flowing fluid streams forming the test mixture stream is continuously and linearly varied with time by alteration of the relative proportion of the component streams forming the test mixture, whilst the total volume of the test mixture stream remains constant.

15. A method according to claim 14, wherein the spectrophotometric detection zone comprises a multiwavelength spectrophotometric detector.

16. A method according to claim 15 wherein the spectrophotometric detector is an ultraviolet or visible range spectrophotometer, a fluorimeter, a polarimeter, a colourimeter, or a light scattering, optical rotation or circular dichrosim detector.

17. A method according to claim 16, wherein the spectrophotometric detector is a scanning ultraviolet or visible range spectrophotometer.

* * * * *